US011160814B1

(12) United States Patent
Kuo

(10) Patent No.: US 11,160,814 B1
(45) Date of Patent: Nov. 2, 2021

(54) METHODS OF TREATMENT FOR DISEASE FROM CORONAVIRUS EXPOSURE

(71) Applicant: Ensemble Group Holdings, Scottsdale, AZ (US)

(72) Inventor: Michael David Kuo, Scottsdale, AZ (US)

(73) Assignee: ENSEMLBLE GROUP HOLDINGS, Scottsdale, AZ (US)

(*) Notice: Subject to any disclaimer, the term of this patent is extended or adjusted under 35 U.S.C. 154(b) by 0 days.

(21) Appl. No.: 17/194,931

(22) Filed: Mar. 8, 2021

Related U.S. Application Data

(60) Provisional application No. 63/063,149, filed on Aug. 7, 2020, provisional application No. 63/021,544, filed on May 7, 2020.

(51) Int. Cl.
| | | |
|---|---|---|
| *A61K 31/58* | (2006.01) | |
| *A61K 31/167* | (2006.01) | |
| *A61K 31/567* | (2006.01) | |
| *A61K 31/137* | (2006.01) | |
| *A61P 11/16* | (2006.01) | |
| *A61K 31/40* | (2006.01) | |
| *A61K 31/4704* | (2006.01) | |
| *A61K 31/381* | (2006.01) | |
| *A61K 31/522* | (2006.01) | |
| *A61K 45/06* | (2006.01) | |
| *A61K 31/439* | (2006.01) | |
| *A61K 31/404* | (2006.01) | |

(52) U.S. Cl.
CPC ............ *A61K 31/58* (2013.01); *A61K 31/137* (2013.01); *A61K 31/167* (2013.01); *A61K 31/381* (2013.01); *A61K 31/40* (2013.01); *A61K 31/404* (2013.01); *A61K 31/439* (2013.01); *A61K 31/4704* (2013.01); *A61K 31/522* (2013.01); *A61K 31/567* (2013.01); *A61K 45/06* (2013.01); *A61P 11/16* (2018.01)

(58) Field of Classification Search
CPC ........ A61K 31/56; A61K 47/02; A61K 47/10; A61K 47/186; A61K 47/26; A61K 47/46; A61K 9/0043; A61K 31/4402; A61P 31/14
See application file for complete search history.

(56) References Cited

U.S. PATENT DOCUMENTS

| 10,022,326 | B2 | 7/2018 | Chu |
| 10,537,586 | B2 | 1/2020 | Altschul |
| 2009/0035375 | A1 | 2/2009 | Skrtic |

OTHER PUBLICATIONS

Arnold, D. et al., "Patient Outcomes After Hospitalisation With COVID-19 and Implications for Follow-Up: Results From a Prospective UK Cohort", Thorax., 2020-216086, pp. 1-4, (2020).
Bacci, E. et al., "Evaluation of a Respiratory Symptom Diary for Clinical Studies of Idiopathic Pulmonary Fibrosis", Respir Med., 134:130-8, (2018).
Cheng, P. et al., "Viral Shedding Patterns of Coronavirus in Patients With Probable Severe Acute Respiratory Syndrome", Lancet, 363(9422):1699-700, (2004).
Covid-Miner, https://covid-miner.ifo.gov.it/app/variants (last visited Mar. 4, 2021).
Doull, I. et al., "Effect of Inhaled Corticosteroids on Episodes of Wheezing Associated With Viral Infection in School Age Children: Randomised Double Blind Placebo Controlled Trial", BMJ., 315(7112):858-62, (1997).
Gandhi, M. et al., "Asymptomatic Transmission, the Achilles' Heel of Current Strategies to Control Covid-19", N Engl J Med., 382(22):2158-60, (2020).
Genomic epidemiology of novel coronavirus—Global subsampling, https://nextstrain.org/ncov/global (last visited Mar. 4, 2021).
Gisaid, https://www.gisaid.org (last visited Mar. 4, 2021).
Global.health, https://global.health (last visited Mar. 4, 2021).
Hanania, N et al., "Adverse Effects of Inhaled Corticosteroids", Am J Med., 98(2):196-208, (1995).
Hoover, John E., Remington's Pharmaceutical Sciences, Mack Publishing Co., Easton, PA, 1975.
Huang, C. et al., "6-Month Consequences of COVID-19 in Patients Discharged From Hospital: A Cohort Study", Lancet, 397(10270):220-32, (2021).
Ip, D. et al., "Viral Shedding and Transmission Potential of Asymptomatic and Paucisymptomatic Influenza Virus Infections in the Community", Clin Infect Dis., 64(6):736-42, (2017).
Kibbe, et al., Eds., Handbook of Pharmaceutical Excipients (3rd Ed.), American Pharmaceutical Association, Washington, 1999.
Liberman, et al., Eds., Pharmaceutical Dosage Forms, Marcel Decker, New York, NY, 1980.
Logue, J. et al., "Sequelae in Adults at 6 Months After COVID-19 Infection", JAMA Netw Open., 4(2):e210830, pp. 1-4; (2021).
Lui, G. et al., "Viral Dynamics of SARS-CoV-2 Across a Spectrum of Disease Severity in COVID-19", J Infect., 81 (2):318-56, (2020).
McCarthy, K. et al., "Recurrent Deletions in the SARS-CoV-2 Spike Glycoprotein Drive Antibody Escape", Science, eabf6950, (2021).
Pulmocort Turbuhaler, https://www.rxlist.com/pulmicort-turbuhaler-drug.htm, (last viewed Mar. 4, 2021).
Ramakrishnan et al., "Inhaled Budesonide in the Treatment of Early COVID-19 Illness: A Randomized Controlled Trial", Medrxiv Preprint, https://doi.org/10.1101/2021.02.04.21251134, last updated Feb. 8, 2021.
SARS-CoV-2 Variants, US Centers for Disease Control and Prevention, https://www.cdc.gov/coronavirus/2019-ncov/cases-updates/variant-surveillance/variant-info.html (last updated Jan. 31, 2021).
Stahl, P. et al., "Pharmaceutical Salts: Properties, Selection, and Use", Wiley-VCHA, Zurich, Switzerland, (2002).
To, K. et al., "Temporal Profiles of Viral Load in Posterior Oropharyngeal Saliva Samples and Serum Antibody Responses During Infection by SARS-CoV-2: An Observational Cohort Study", Lancet Infect Dis., 20(5):565-74, (2020).
Weiss, A. et al., "Spatial and Temporal Dynamics of SARS-CoV-2 in COVID-19 Patients: A Systematic Review and Meta-Analysis", EBioMedicine, 58:102916, (2020).

(Continued)

*Primary Examiner* — Savitha M Rao
(74) *Attorney, Agent, or Firm* — Global Patent Group, LLC; Dennis Bennett; Ca Schlecht

(57) ABSTRACT

Disclosed herein are methods of treating a disease in a subject which is the consequence of previous exposure of the subject to a virus, particularly SARS-CoV-2, the method comprising administration of an effective amount of one or more agents to the subject.

22 Claims, No Drawings

(56) References Cited

OTHER PUBLICATIONS

Wölfel, R. et al., "Virological Assessment of Hospitalized Patients With COVID-2019", Nature, 581(7809):465-9, (2020).
Zheng, S. et al., "Viral Load Dynamics and Disease Severity in Patients Infected With SARS-CoV-2 in Zhejiang Province, China, Jan.-Mar. 2020: Retrospective Cohort Study", BMJ., 369:m1443, (2020).
Zou, L. et al., "SARS-CoV-2 Viral Load in Upper Respiratory Specimens of Infected Patients", N Engl J Med., 382 (12):1177-9, (2020).
Aberdein, J. et al., "Clinical review: a systematic review of corticosteroid use in infections", Crit Care, 10(1):1-10, (2006).
Anonymous, "Shingles", Wikipedia, Retrieved from https://en.wikipedia.org/w/index.php?title=Shingles&oldid=1039648767 on Aug. 19, 2021; 22 pages.
Arnold, D. et al., "Patient outcomes after hospitalisation with COVID-19 and implications for follow-up; results from a prospective UK cohort", medRxiv preprint, 19 pages, (2020).
Aronson, K. et al., "Lungs after COVID-19: Evolving Knowledge of Post-COVID-19 Interstitial Lung Disease", Ann Am ThoracSoc., 18(5):773-4, (2021.
Carfi, A. et al., "Persistent Symptoms in Patients After Acute COVID-19", JAMA, 324(6):E1-2, (2020).
ClinicalTrials.gov, "Evaluation of Efficacy of Levamisole and Formoterol+Budesonide in Treatment of COVID-19", Apr. 13, 2020 (Apr. 13, 2020), retrieved on Jul. 6, 2021 from https://clinicaltrials.gov/ct2/show/NCT04331470.
Huang, Y. et al., "Impact of coronavirus disease 2019 on pulmonary function in early convalescence phase", Respir Res., 21(1): 163, 10 pages, (2020).
International Application No. PCT/US2021/031162; International Search Report and Written Opinion of the International Searching Authority, dated Aug. 12, 2020; 7 pages.
Myall, K. et al., "Persistent Post-COVID-19 Interstitial Lung Disease. An Observational Study of Corticosteroid Treatment", Ann Am Thorac Soc., 18(5):799-806, (2021).
Nalbandian, A. et al., "Post-acute COVID-19 syndrome", Nat Med., 27(4):601-15, (2021).
Ramakrishnan, S. et al., "Inhaled budesonide in the treatment of early COVID-19 (STOIC): a phase 2, open-label, randomised controlled trial", Lancet Respir Med., 9(7):763-72, (2021).
Russell, C. et al., "Clinical evidence does not support corticosteroid treatment for 2019-nCoV lung injury", Lancet, 395(10223):473-5, (2020).
Vasarmidi, E. et al., "Pulmonary fibrosis in the aftermath of the COVID-19 era (Review)", Exp Ther Med., 20(3):2557-60, (2020).
Yang, J. et al., "Corticosteroid administration for viral pneumonia: COVID-19 and beyond", Clin Microbiol Infect., 26(9):1171-7, (2020).
Yang, J. et al., "Corticosteroids for the treatment of human infection with influenza virus: a systematic review and meta-analysis", Clin Microbiol Infect., 21(10):956-63, (2015).
Yu, L. et al., "Inhaled budesonide for COVID-19 in people at higher risk of adverse outcomes in the community: interim analyses from the PRINCIPLE trial", medRxiv, 43 pages, (2021).

METHODS OF TREATMENT FOR DISEASE FROM CORONAVIRUS EXPOSURE

This application claims the benefit of priority of U.S. Provisional Patent Application Ser. No. 63/021,544 filed May 7, 2020, and also claims the benefit of priority of the U.S. Provisional Patent Application Ser. No. 63/063,149 filed Aug. 7, 2020, the disclosures of which are each incorporated by reference in their entireties for all purposes.

The worldwide COVID-19 pandemic rivals the 1918 influenza outbreak as the most significant health crisis in modern society. Although COVID-19, caused by the SARS-CoV-2 virus, has been observed to impact the heart and kidneys, and the nervous and digestive system, the disease predominantly impacts the respiratory system. Although the disease can remain undetected after infection for days or weeks before presenting symptoms, its effects on morbidity and mortality generally manifest quickly once the disease takes hold. Subjects will often present with gastrointestinal symptoms; however, the most common symptoms are fever, cough, and shortness of breath. Outcomes from infection span a wide range: an unknown fraction of subjects exposed to the virus do not present with any symptoms, some people experience mild to moderate symptoms akin to a cold or the flu, and a fraction of subjects experience a crisis that requires hospitalization, with oxygen treatment and often intubation often being necessary to overcome damage to the lungs.

Because the virus has only recently been encountered, very little is known about the effects of infection by the SARS-CoV-2 virus on survivors' long-term health. In the United Kingdom, up to 20% of patients reported persistent symptoms five weeks after COVID-19. This finding suggests that intervention with inhaled glucocorticoids might impact the rate of persistent long-term symptoms in COVID-19 ("long COVID"). Long-term pulmonary effects, blood disorders, and neurological damage are possible; however, both the newness of the disease and the lack of knowledge of the particular impact of the virus on the body and the survivor population's demographics make definitive predictions impossible.

Due to the widespread penetration of this disease and the concomitant number of survivors from all degrees of illness, many sequelae will likely emerge over the coming months and years. Understandably, attention has been mostly directed at compounds and methods for treating acute COVID-19. However, treating the long-term ailments derived from exposure to SARS-CoV-2 will increasingly be required.

BRIEF DESCRIPTION

Provided herein is a method of treating a pulmonary disease which is the consequence of previous exposure of a subject to a severe acute respiratory syndrome coronavirus-2 (SARS-CoV-2), the method comprising administering to the subject of an effective amount of one or more corticosteroids.

In certain embodiments, the one or more corticosteroids are chosen from hydrocortisone, methylprednisolone, budesonide, beclomethasone, fluticasone, fluticasone furoate, fluticasone propionate, mometasone, mometasone furoate, and vamorolone, such as budesonide, any of which can be administered twice daily.

In certain embodiments, the one or more corticosteroids are administered immediately after exposure to SARS-CoV-2 before initial recovery. In certain embodiments, the one or more corticosteroids are administered immediately after exposure to SARS-CoV-2 after peak disease severity during recovery. In certain embodiments, the one or more corticosteroids are administered after viral recovery. In certain embodiments, the one or more corticosteroids are administered or maintained continuously. In certain embodiments, the one or more corticosteroids are administered when the subject expresses a symptom which is a consequence of the previous exposure of the SARS-CoV-2 or is about to partake in an activity that may precipitate the symptom. In certain embodiments, the one or more corticosteroids are administered in any combination of these aforementioned dosing schedules.

In certain embodiments, the method further comprises administering one or more leukotriene antagonists, such as zafirlukast, montelukast, and zileuton. In certain embodiments, the method further comprises administering one or more beta-agonists. In certain embodiments, the method further comprises administering one or more methylxanthines, such as theophylline, dyphylline, and aminophylline. In certain embodiments, the method further comprises administering one or more bronchodilators, for example, an anticholinergic or an antimuscarinic, such as tiotropium, ipratropium, aclidinium, glycopyrronium, and/or salts thereof. In certain embodiments, the one or more bronchodilators comprises a beta-2 agonist, such as salbutamol, albuterol, salmeterol, and formoterol.

In certain embodiments, the exposure of the subject to the SARS-CoV-2 virus is confirmed by a positive titer for the SARS-CoV-2, by a positive titer for antibodies to the SARS-CoV-2, or by one or more recognized clinical symptoms associated with infection by SARS-CoV-2. In certain embodiments, the one or more recognized clinical symptoms are chosen from cough, shortness of breath, difficulty breathing, asthma, fever, chills, repeated shaking, muscle pain, headache, sore throat, loss of taste, loss of smell, blood clotting, stroke, pernio, and chilblain (so-called "covid toes").

The present disclosure also provides a method of reducing, delaying the onset of, or preventing symptoms which are the consequence of previous exposure of a subject to a severe acute respiratory syndrome coronavirus-2 (SARS-CoV-2), the method comprising administering to the subject of an effective amount of one or more corticosteroids.

DETAILED DESCRIPTION

SARS-CoV-2 (hereafter referenced as "SARS2", "COVID-19" or "COVID") was first reported in December 2019 in Wuhan, China, with first published reports emerging in January of 2020. While it is a member of the coronavirus family and initially known to cause viral pneumonia, the art initially taught that it was generally similar to other pulmonary-tropic coronaviruses, except less contagious and less deadly than other recent coronavirus outbreaks, namely SARS-CoV-1 and MERS-CoV (hereafter referenced as "SARS1" and "MERS" respectively).

It is now becoming increasingly clear that COVID infections are very distinct from other coronavirus infections. As described herein, SARS-CoV-2's viral transmission kinetics, patterns, duration, and time to peak of viral shedding, R naught (abbreviated Ro), number of viral particles in different body compartments, and clinical natural history, among many other factors, are profoundly different from SARS and MERS, and other viruses in general, such as influenza, which SARS-CoV-2 was also initially compared to. Critically, although SARS1 and MERS are members of the same viral family as COVID, all infecting the lungs, any attempt to project acute, intermediate, and long-term consequences from SARS2 infection, as has been described herein, are complete guesswork. For example, the clinical and laboratory manifestations of SARS2 are far different from SARS1, MERS, and other viral pneumonia, with symptoms of headaches, loss of smell, multi-system inflammatory syndromes in children, myocarditis, pulmonary hypertension, thromboembolic disorders, stroke, renal failure, high serum levels of ferritin, LDH, and C-reactive protein, distinct serum immune signature as well as metabolite profiles, among a host of other phenomena that all clearly distinguish SARS2 from SARS2, MERS, and other viral pneumonia, and thus reinforcing the fact that forecasting of acute, intermediate and long term sequelae of the disease without any comparable precedent, complete guesswork at this time.

To date, almost all studies have focused on investigating and treating severe and hospitalized COVID-19 infection. However, there is currently little knowledge on therapeutic targets in early COVID-19 infection or during or after recovery to subsequently prevent or mitigate progression and clinical deterioration. Early reports describing COVID-19 infection from China, Italy, and the United States significantly underrepresented the number of patients with asthma and chronic obstructive pulmonary disease (COPD). In-vitro studies have shown that inhaled glucocorticoids reduce SARS-CoV-2 replication in airway epithelial cells and downregulated the expression of angiotensin-converting enzyme-2 (ACE2) and transmembrane protease serine 2 (TMPRSS2) genes, which are critical for viral cell entry.

Herein is disclosed that, contrary to the art, SARS2 has unique and unprecedented immediate recovery and convalescent-phase, intermediate phase, and long-term phase clinical sequelae upon previously SARS2 infected patients that affect the lungs both physically and structurally as well as functionally and physiologically. These effects can be mitigated with both specific treatments and formulations and delivery methods and the timing of their delivery and in which patient populations said such treatments are tailored for delivery to.

As disclosed herein, in a cohort of clinically recovered SARS2 patients, with follow-up from as little as 1-week post medically deemed clinical recovery to as far as 6 months out, greater than 15% of these patients presented evidence by medical imaging-chest x-ray and CT of long-lasting structural lung damage, including but not limited: to volume loss and fibrosis and scarring affecting the pulmonary parenchyma as well as small, medium and large airways, as well as the pleura, pulmonary interstitium and secondary lobules (including centrilobular and perilymphatic areas). Additionally, varying degrees of ground-glass opacities, traction on airways, distorted architectural interfaces, consolidation, and interstitial thickening was observed over time, and this was independent of clinical severity of the SARS2 active phase infection, length of hospital duration, and available treatments administered at that time (oxygen support— including ECMO, positive pressure air support, or mechanical ventilation, or medical/pharmacologic treatment including antiviral therapies or steroids or broad or targeted anti-inflammatory or immune-modulating agents).

Further, similar changes were observed in objective pulmonary function as measured by objective testing measures as described below, and clinical symptoms with patients demonstrating persistent and unresolved fatigue and airway reactivity that was both generalized as well as activity mediated (including exercise mediated or exertional) as well as hypersensitized to previously tolerated stimuli or antigens. Further, patients demonstrated persistent, slowly resolving, or progressively worsening dyspnea, shortness of breath, persistent or intermittent dry and wet or productive cough as well as drops in arterial blood gases, oxygen content, and saturation, oxygen diffusivity, or gas exchange.

As disclosed below, in a cohort of clinically recovered SARS2 patients, with follow-up from as little as 1-week post medically deemed clinical recovery to as far as 6 months out, greater than 30% of these patients had evidence of long-lasting functional lung damage or loss in pulmonary capacity or reserve which was observed over time and which was independent of clinical severity of the SARS2 active phase infection, length of hospital duration, and available treatments administered at that time (oxygen support— including ECMO, positive pressure air support, or mechanical ventilation, or medical/pharmacologic treatment including antiviral therapies or steroids or broad or targeted anti-inflammatory or immune-modulating agents). Testing measures to assess this included the methods described below.

As discussed by Gandhi, M., et al., *Asymptomatic transmission, the Achilles' heel of current strategies to control COVID-19*, 382 NEW ENG. J. MED., 2158-2160 (2020), a key factor in the transmissibility of COVID-19 is the high level of SARS-CoV-2 shedding in the upper respiratory tract (versus SARS-CoV1 and MERS-CoV, which are primarily lower respiratory tract tropic) even among presymptomatic patients, which distinguishes it from SARS-CoV-1, where replication occurs mainly in the lower respiratory tract. See Wölfel, R., et al., *Virological assessment of hospitalized patients with COVID-2019*, 581 NATURE 465-469 (2020); and Cheng, P. K., et al., *Viral shedding patterns of coronavirus in patients with probable severe acute respiratory syndrome*, 363 LANCET 1699, 1699-1700 (2004). Viral loads with SARS-CoV-1, which are associated with symptom onset, peak a median of 5 days later than viral loads with SARS-CoV-2, which makes symptom-based detection of infection more effective in the case of SARS CoV-1. To, K. K. W., et al., *Temporal profiles of viral load in posterior oropharyngeal saliva samples and serum antibody responses during infection by SARS-CoV-2: an observational cohort study*, 20 LANCET INFECTIOUS DISEASES, P565-574 (2020), available at https://www.thelancet.com/journals/laninf/article/PIIS1473-3099(20)30196-1/fulltext. With influenza, persons with the asymptomatic disease generally have lower quantitative viral loads in secretions from the upper respiratory tract than from the lower respiratory tract and a shorter duration of viral shedding than persons with symptoms which decreases the risk of transmission from paucisymptomatic persons (i.e., those with few symptoms).

Ip, D. K., et al., *Viral shedding and transmission potential of asymptomatic and paucisymptomatic influenza virus infections in the community*, 64 CLINICAL INFECTIOUS DISEASES, 736-742 (2017) reported that more than half the residents of this skilled nursing facility (27 of 48) who had positive tests were asymptomatic at testing. Moreover, live coronavirus sheds at high concentrations from the nasal cavity even before symptom development.

Unlike SARS1 and MERS, COVID has a large proportion of completely asymptomatic patients prone to a high transmission before developing symptoms, viral loads peak earlier and taper slower and later, has a much smaller proportion of patients who require treatment or hospitalization, and a far lower fatality rate. Below are additional data that highlight characteristics of SAR2.

SARS2 Variants

The SARS2 virus continues to mutate and present new variants in the human population. Examples of clinically concerning strains include B1.526, also called the New York variant, which includes LSF, T95I, D253G, E484K, S477N, D614G, and A701V among other mutations, B.1.427/B.1.429/20C/L452R, also called CAL.20, in California, B.1.1.7 in the United Kingdom (UK), B.1.351 in South Africa, and P.1 in Brazil. See *SARS-CoV-2 Variants*, US CENTERS FOR DISEASE CONTROL AND PREVENTION, https://www.cdc.gov/coronavirus/2019-ncov/cases-updates/variant-surveillance/variant-info.html (last updated Jan. 31, 2021). At least four large databases have sequenced the SARS-CoV-2 virus and listed variants by time, clade, country, etc. See *GISAID*, https://www.gisaid.org (last visited Mar. 4, 2021); *Covid-Miner*, https://covid-miner.ifo.gov.it/app/variants (last visited Mar. 4, 2021); *Genomic epidemiology of novel coronavirus—Global subsampling*, https://nextstrain.org/ncov/global (last visited Mar. 4, 2021); and *Global.health*, https://global.health (last visited Mar. 4, 2021).

In the UK is a variant of SARS-CoV-2 known as B.1.1.7 emerged. This variant carries many mutations and has since been detected around the world, including in the United States (US). This variant was first detected in the US at the end of December 2020. In January 2021, scientists from the UK reported early evidence that suggests the B.1.1.7 variant may be associated with an increased risk of death compared with other variants.

In South Africa, another variant of SARS-CoV-2 known as B.1.351 emerged independently of B.1.1.7. According to a non-peer-reviewed preprint article, this variant shares some mutations with B.1.1.7. Cases attributed to B.1.351 have been detected outside of South Africa, and this variant was first detected in the US at the end of January 2021. Preliminary evidence from non-peer-reviewed publications suggests that the Moderna mRNA-1273 vaccine currently used in the US may be less effective against this variant.

In Brazil, a variant of SARS-CoV-2 known as P.1 emerged; it was first identified in January 2021 in travelers from Brazil who arrived in Japan. This variant was detected in the US at the end of January 2021. The P.1 variant has 17 unique mutations, including three in the receptor-binding domain of the spike protein (K417T, E484K, and N501Y), according to non-peer-reviewed preprint articles. There is evidence to suggest that some of the mutations in the P.1 variant may affect the ability of antibodies (from natural infection or vaccination) to recognize and neutralize the virus.

In certain embodiments, the subject was previously exposed to the B1.526 variant of SARS-CoV-2. In certain embodiments, the subject was previously exposed to the B.1.427/B.1.429/20C/L452R (CAL.20) variant of SARS-CoV-2. In certain embodiments, the subject was previously exposed to the B.1.1.7 variant of SARS-CoV-2. In certain embodiments, the subject was previously exposed to the B.1.351 variant of SARS-CoV-2. In certain embodiments, the subject was previously exposed to the P.1 variant of SARS-CoV-2.

Concerning mutations in the B.1.17 variant are the 69/70 deletion, 144Y deletion, N501Y, A570D, D614G, and P681H. Concerning mutations in the P.1 variant are E484K, K417N/T, N501Y, and D614G. Concerning mutations in the B.1.351 variant are K417N, E484K, N501Y, and D614G.

One specific mutation, called D614G, is shared by these three variants. It gives the variants the ability to spread more quickly than the predominant viruses. There also is epidemiologic evidence that variants with this specific mutation spread more quickly than viruses without the mutation. This mutation was one of the first documented in the US in the pandemic's initial stages, after having first circulated in Europe. See McCarthy et al., *Recurrent deletions in the SARS-CoV-2 spike glycoprotein drive antibody escape*, SCIENCE 10.1126/science.abf6950 (2021), available at https://science.sciencemag.org/content/early/2021/02/02/science.abf6950.

In certain embodiments, the subject was previously exposed to a variant of SARS-CoV-2 having one or more mutations chosen from 69/70 deletion, 144Y deletion, N501Y, A570D, D614G, P681H, E484K, K417N/T, K417N, and D614G. In certain embodiments, the subject was previously exposed to a variant of SARS-CoV-2 having one or more mutations chosen from N501Y, E484K, K417N/T, and D614G. In certain embodiments, the subject was previously exposed to a variant of SARS-CoV-2 having a D614G mutation.

EXEMPLARY EMBODIMENTS

Provided herein are the following specific embodiments:

Embodiment 1. A method of treating a pulmonary disease which is the consequence of previous exposure of a subject to a severe acute respiratory syndrome coronavirus-2 (SARS-CoV-2), the method comprising administration to the subject of an effective amount of one or more agents chosen from antiasthmatics, bronchodilators, and tyrosine kinase inhibitors.

Embodiment 2. The method as recited in Embodiment 1, wherein the one or more agents comprises one or more antiasthmatics.

Embodiment 3. The method as recited in Embodiment 2, wherein the one or more antiasthmatics comprises a corticosteroid.

Embodiment 4. The method as recited in Embodiment 3, wherein the corticosteroid is chosen from hydrocortisone, methylprednisolone, budesonide (PULMICORT®, RHINOCORT®, ENTOCORT®), beclomethasone (QVAR®), fluticasone, fluticasone furoate (ARNUITY® ELLIPTA®), fluticasone propionate (FLOVENT®, FLONASE®, FLIXOTIDE), mometasone, mometasone furoate (NASONEX®, ASMANEX®, ELOCON®), and vamorolone.

Embodiment 5. The method as recited in any one of Embodiments 2-4, wherein the one or more antiasthmatics comprises a leukotriene antagonist.

Embodiment 6. The method as recited in Embodiment 5, wherein the leukotriene antagonist is chosen from zafirlukast (ACCOLATE®), montelukast (SINGULAIR®), and zileuton (ZYFLO®).

Embodiment 7. The method as recited in any one of Embodiments 2-6, wherein the one or more antiasthmatics comprises a beta agonist.

Embodiment 8. The method as recited in any one of Embodiments 2-7, wherein the one or more antiasthmatics comprises a methylxanthine.

Embodiment 9. The method as recited in Embodiment 8, wherein the methylxanthine is chosen from theophylline, dyphylline, and aminophylline.

Embodiment 10. The method as recited in any one of Embodiments 1-9, wherein the one or more agents comprises one or more bronchodilators.

Embodiment 11. The method as recited in Embodiment 10, wherein the one or more bronchodilators comprises an anticholinergic.

Embodiment 12. The method as recited in either one of Embodiments 10 and 11, wherein the one or more bronchodilators comprises an antimuscarinic.

Embodiment 13. The method as recited in Embodiment 12, wherein the antimuscarinic is chosen from tiotropium (SPIRIVA®), ipratropium (ATROVENT®), aclidinium (BRETARIS® GENUAIR, EKLIRA GENUAIR, TUDORZA® PRESSAIR®), and glycopyrronium (ROBINUL, CUVPOSA®, SEEBRI®).

Embodiment 14. The method as recited in any one of Embodiments 10-13, wherein the one or more bronchodilators comprises a beta-2 agonist.

Embodiment 15. The method as recited in Embodiment 14, wherein the beta-2 agonist is chosen from salbutamol (albuterol, VENTOLIN®) and salmeterol (SEREVENT®, AEROMAX).

Embodiment 16. The method as recited in Embodiment 1, wherein the one or more agents comprises a tyrosine kinase inhibitor.

Embodiment 17. The method as recited in Embodiment 16, wherein the tyrosine kinase inhibitor has inhibitory activity towards one or more receptors chosen from platelet-derived growth factor (PDGF), fibroblast growth factor receptor 1 (FGFR1), fibroblast growth factor receptor 2 (FGFR2), fibroblast growth factor receptor 3 (FGFR3), vascular endothelial growth factor receptor 1 (VEGFR1), vascular endothelial growth factor receptor 2 (VEGFR2), and vascular endothelial growth factor receptor 3 (VEGFR3).

Embodiment 18. The method as recited in Embodiment 16, wherein the tyrosine kinase inhibitor is nintedanib (OFEV®).

Embodiment 19. The method as recited in Embodiment 16, wherein the tyrosine kinase inhibitor is pirfenidone (ESBRIET®, PIRESPA®, ETUARY®).

Embodiment 20. A method of reducing pulmonary symptoms which are the consequence of previous exposure of a subject to a severe acute respiratory syndrome coronavirus-2 (SARS-CoV-2), the method comprising administration to the subject of an effective amount of one or more agents chosen from antiasthmatics, bronchodilators, and tyrosine kinase inhibitors.

Embodiment 21. A method of delaying the onset of pulmonary symptoms which are the consequence of previous exposure of a subject to a severe acute respiratory syndrome coronavirus-2 (SARS-CoV-2), the method comprising administration to the subject of an effective amount of one or more agents chosen from antiasthmatics, bronchodilators, and tyrosine kinase inhibitors.

Embodiment 22. A method of preventing pulmonary symptoms which are the consequence of previous exposure of a subject to a severe acute respiratory syndrome coronavirus-2 (SARS-CoV-2), the method comprising administration to the subject of an effective amount of one or more agents chosen from antiasthmatics, bronchodilators, and tyrosine kinase inhibitors.

Embodiment 23. The method as recited in any one of Embodiments 20-21, wherein the symptoms are chosen from cough, shortness of breath, difficulty breathing, asthma, fever, chills, repeated shaking, muscle pain, headache, sore throat, loss of taste, loss of smell, bloodclotting, stroke, pernio, and chilblain.

Embodiment 24. The method as recited in any one of Embodiments 1-23, wherein the exposure of the subject to the SARS-CoV-2 virus is confirmed by a positive titer for the SARS-CoV-2.

Embodiment 25. The method as recited in any one of Embodiments 1-23, wherein the exposure of the subject to the SARS-CoV-2 virus is confirmed by a positive titer for antibodies to the SARS-CoV-2.

Embodiment 26. The method as recited in any one of Embodiments 1-23, wherein the exposure of the subject to the SARS-CoV-2 virus is confirmed by one or more recognized clinical symptoms associated with infection by SARS-CoV-2.

Agents

In certain embodiments, the one or more agents comprise one or more antiasthmatics. In certain embodiments, the one or more antiasthmatics comprises a corticosteroid. In certain embodiments, the corticosteroid is chosen from hydrocortisone, methylprednisolone, budesonide (Pulmicort®, Rhinocort®, Entocort®), beclomethasone (Qvar®), fluticasone, fluticasone furoate (Arnuity® Ellipta®), fluticasone propionate (Flovent®, Flonase®, Flixotide), mometasone, mometasone furoate (Nasonex®, Asmanex®, Elocon®), and vamorolone. In certain embodiments, the one or more antiasthmatics comprises a leukotriene antagonist. In certain embodiments, the leukotriene antagonist is chosen from zafirlukast (Accolate®), montelukast (Singulair®), and zileuton (Zyflo®). In certain embodiments, the one or more antiasthmatics comprises a beta-agonist, such as a long-acting beta-agonist. In certain embodiments, the one or more antiasthmatics comprise a methylxanthine. In certain embodiments, the methylxanthine is chosen from theophylline, dyphylline, and aminophylline.

In certain embodiments, the one or more agents comprises one or more bronchodilators. In certain embodiments, the one or more bronchodilators comprises an anticholinergic. In certain embodiments, the one or more bronchodilators comprises an antimuscarinic. In certain embodiments, the muscarinic is chosen from tiotropium (Spiriva®), ipratropium (Atrovent®), aclidinium (Bretaris® Genuair, Eklira Genuair, Tudorza® Pressair®), and glycopyrronium (Robinul, Cuvposa®, Seebri®). In certain embodiments, the one or more bronchodilators comprises a beta-2 agonist. In certain embodiments, the beta-2 agonist is chosen from salbutamol (albuterol, Ventolin®) and salmeterol (Serevent®, Aeromax).

In certain embodiments, the one or more agents comprise a tyrosine kinase inhibitor. In certain embodiments, the tyrosine kinase inhibitor has inhibitory activity towards one or more receptors chosen from platelet-derived growth factor (PDGF), fibroblast growth factor receptor 1 (FGFR1), fibroblast growth factor receptor 2 (FGFR2), fibroblast growth factor receptor 3 (FGFR3), vascular endothelial growth factor receptor 1 (VEGFR1), vascular endothelial growth factor receptor 2 (VEGFR2), and vascular endothelial growth factor receptor 3 (VEGFR3). In certain embodiments, the tyrosine kinase inhibitor is Nintedanib (OFEV®). In certain embodiments, the tyrosine kinase inhibitor is pirfenidone (ESBRIET®, PIRESPA®, ETUARY®).

In certain embodiments, the medicament is a corticosteroid. In certain embodiments, the corticosteroid is chosen from beclomethasone, budesonide, fluticasone, and mometasone.

In certain embodiments, the corticosteroid is administered alone. In certain embodiments, the corticosteroid is administered in combination with any other number of corticosteroids at any of the doses disclosed and can be administered up to 8 times per day. Any of the aforementioned Beta2 adrenoreceptor agonists (including the aforementioned LABAs and ultraLABAs) can be administered alone or in combination with any other number of Beta2 adrenoreceptor agonists at any of the doses disclosed and can be administered up to 8 times per day. Any of the aforementioned corticosteroid, beta2 adrenoreceptor agonist, and tyrosine kinase antagonist listed can be administered or delivered in any combination at any of the doses disclosed. They can be administered up to 8 times per day.

In certain embodiments, the medicament is beclomethasone. In certain embodiments, the dosage of beclomethasone is delivered by any one of the following methods: aerosol, nebulized, powder, metered, and inhalation. In certain embodiments, the dosage of beclomethasone is delivered via inhalation. In certain embodiments, the dosage of beclomethasone is any one of 20, 30, 40, 50, 60, 70, 80, 90, 100, 110, 120, 130, 140, 150, 160, 170, 180, 190, 200 mg. In certain embodiments, the dosage of beclomethasone is 40 mg. In certain embodiments, the dosage of beclomethasone is 80 mg.

In certain embodiments, the medicament is budesonide. In certain embodiments, the dosage of budesonide is delivered by any one of the following methods: aerosol, nebulized, powder, metered, and inhalation. In certain embodiments, the dosage of budesonide is delivered via inhalation. In certain embodiments, the dosage of budesonide is any one of 0.040, 0.045, 0.050, 0.055, 0.060, 0.065, 0.070, 0.075, 0.080, 0.085, 0.090, 0.095, 0.100, 0.105, 0.110, 0.115, 0.120, 0.125, 0.130, 0.135, 0.140, 0.145, 0.150, 0.155, 0.160, 0.165, 0.170, 0.175, 0.180, 0.185, 0.190, 0.195, 0.200, 0.205, 0.210, 0.215, 0.220, 0.225, 0.230, 0.235, 0.240, 0.245, 0.250, 0.255, 0.260, 0.265, 0.270, 0.275, 0.280, 0.285, 0.290, 0.295, 0.300, 0.305, 0.310, 0.315, 0.320, 0.325, 0.330, 0.335, 0.340, 0.345, 0.350, 0.355, 0.360, 0.365, 0.370, 0.375, 0.380, 0.385, 0.390, 0.395, 0.400, 0.405, 0.410, 0.415, 0.420, 0.425, 0.430, 0.435, 0.440, 0.445, 0.450, 0.455, 0.460, 0.465, 0.470, 0.475, 0.480, 0.485, 0.490, 0.495, and 0.500 mg. In certain embodiments, the dosage of budesonide is 0.080 mg. In certain embodiments, the dosage of budesonide is 0.160 mg. In certain embodiments, the dosage of budesonide is 0.320 mg.

In certain embodiments, the medicament is fluticasone propionate. In certain embodiments, the dosage of fluticasone propionate is delivered by any one of the following methods: aerosol, nebulized, powder, metered, and inhalation. In certain further embodiments, the dosage is delivered via inhalation. In yet further embodiments, the inhaled dosage is any one of 0.1, 0.15, 0.175, 0.2, 0.225, 0.25, 0.275, 0.3, 0.325, 0.35, 0.375, 0.4, 0.425, 0.45, 0.475, 0.5. 0.525, 0.55, 0.575, 0.6, 0.625, 0.65, 0.675, 0.7, 0.725, 0.75. 0.775, or 0.8 mg.

In certain embodiments, the medicament is mometasone. In certain embodiments, the dosage of mometasone is delivered by any one of the following methods: aerosol, nebulized, powder, metered, and inhalation. In certain embodiments, the dosage of mometasone is delivered via inhalation. In certain embodiments, the dosage of mometasone is any one of 50, 60, 70, 80, 90, 100, 110, 120, 130, 140, and 150 mg. In certain embodiments, the dosage of mometasone is 100 mg.

In certain embodiments, the medicament is fluticasone furoate.

In certain embodiments, the medicament is ciclesonide. In certain embodiments, the dosage of ciclesonide is delivered by any one of the following methods: aerosol, nebulized, powder, metered, and inhalation. In certain embodiments, the dosage of ciclesonide is delivered via inhalation. In certain embodiments, the dosage of ciclesonide is any one of 40, 50, 60, 70, 80, 90, 100, 110, 120, 130, 140, 150, 160, 170, 180, 190, 200, 210, 220, 230, 240, 250, 260, 270, 280, 290, 300, 310, and 320 mg. In certain embodiments, the dosage of ciclesonide is 80 mg. In certain embodiments, the dosage of ciclesonide is 160 mg.

In certain embodiments, the medicament is flunisolide. In certain embodiments, the dosage of flunisolide is delivered by any one of the following methods: aerosol, nebulized, powder, metered, and inhalation. In certain embodiments, the dosage of flunisolide is delivered via inhalation. In certain embodiments, the dosage of flunisolide is any one of 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 500 mg. In certain embodiments, the dosage of flunisolide is 250 mg.

In certain embodiments, the medicament comprises a combined dosage of mometasone and formoterol fumarate. In certain embodiments, the combined dosage of mometasone and formoterol fumarate is delivered by any one of the following methods: aerosol, nebulized, powder, metered, and inhalation. In certain embodiments, the combined dosage of mometasone and formoterol fumarate is delivered via inhalation. In certain embodiments, the combined dosage of mometasone and formoterol fumarate contains any one of 50, 60, 70, 80, 90, 100, 110, 120, 130, 140, and 150 mg of mometasone. In certain embodiments, the combined dosage of mometasone and formoterol fumarate contains any one of 200, 250, 300, 350, 400, 450, 500, 550, 600, 650, 700, 750 mg of formoterol fumarate.

In certain embodiments, the medicament is a beta2 adrenoreceptor agonist/activator. In certain embodiments, the beta2 adrenoreceptor agonist/activator is chosen from salmeterol, salmeterol xinafoate, formoterol, formoterol fumarate, arformoterol, bambuterol, clenbuterol, protokylol, and albuterol.

In certain embodiments, the medicament is salmeterol xinafoate. In certain embodiments, the dosage of salmeterol xinafoate is delivered by any one of the following methods: aerosol, nebulized, powder, metered, and inhalation. In certain embodiments, the dosage of salmeterol xinafoate is delivered via inhalation. In certain embodiments, the dosage of salmeterol xinafoate is any one of 0.010, 0.020, 0.030, 0.040, 0.050, 0.060, 0.070, 0.080, 0.090, 0.100, 0.110, 0.120, 0.130, 0.140, 0.150, 0.160, 0.170, 0.180, 0.190, 0.200, 0.210, 0.220, 0.230, 0.240, 0.250, 0.260, 0.270, 0.280, 0.290, and 0.300 mg.

In certain embodiments, the medicament is formoterol fumarate. In certain embodiments, the dosage of formoterol fumarate is delivered by any one of the following methods: aerosol, nebulized, powder, metered, and inhalation. In certain embodiments, the dosage of formoterol fumarate is delivered via inhalation. In certain embodiments, the dosage of formoterol fumarate is any one of 0.200, 0.250, 0.300, 0.350, 0.400, 0.450, 0.500, 0.550, 0.600, 0.650, 0.700, 0.750 mg. In certain embodiments, the dosage of formoterol fumarate is 0.450 mg.

In certain embodiments, the medicament is arformoterol. In certain embodiments, the dosage of arformoterol is delivered by any one of the following methods: aerosol, nebulized, powder, metered, and inhalation. In certain embodiments, the dosage of arformoterol is delivered via inhalation. In certain embodiments, the dosage of arformoterol is any one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75 mg. In certain embodiments, the dosage of arformoterol is 15 mg.

In certain embodiments, the medicament is bambuterol. In certain embodiments, the dosage of bambuterol is delivered by any one of the following methods: aerosol, nebulized, powder, metered, and inhalation. In certain embodiments, the dosage of bambuterol is delivered via inhalation. In certain embodiments, the dosage of arformoterol is any one of 5, 10, 15, 20, 25, 30, 35, 40, 45, 50, 55, 60, 65, 70, 75, 80, 85, 90, 95, and 100 mg.

In certain embodiments, the medicament is clenbuterol. In certain embodiments, the dosage of clenbuterol is delivered by any one of the following methods: aerosol, nebulized, powder, metered, and inhalation.

In certain embodiments, the medicament is formoterol. In certain embodiments, the dosage of formoterol is delivered by any one of the following methods: aerosol, nebulized, powder, metered, and inhalation.

In certain embodiments, the medicament is salmeterol. In certain embodiments, the dosage of salmeterol is delivered by any one of the following methods: aerosol, nebulized, powder, metered, and inhalation.

In certain embodiments, the medicament is protokylol. In certain embodiments, the dosage of protokylol is delivered by any one of the following methods: aerosol, nebulized, powder, metered, and inhalation.

In certain embodiments, the medicament is albuterol. In certain embodiments, the dosage of albuterol is delivered by any one of the following methods: aerosol, nebulized, powder, metered, and inhalation.

In certain embodiments, the medicament is an ultra-long-acting β adrenoreceptor agonist (ultra-LABA). In certain embodiments, the ultra-LABA is chosen from indacaterol, olodaterol, and vilanterol.

In certain embodiments, the medicament is indacaterol. In certain embodiments, the dosage of indacaterol is delivered by any one of the following methods: aerosol, nebulized, powder, metered, and inhalation. In certain embodiments, the dosage of indacaterol is delivered via inhalation. In certain embodiments, the dosage of indacaterol is any one of 10, 15, 20, 25, 30, 35, 40, 45, 50, 55, 60, 65, 70, 75, 80, 85, 90, 95, 100, 105, 110, 115, 120, 125, 130, 135, 140, 145, and 150 mg. In certain embodiments, the dosage of indacaterol is 75 mg.

In certain embodiments, the medicament comprises a combined dosage of indacaterol and glycopyrrolate.

In certain embodiments, the medicament is vilanterol. In certain embodiments, the medicament comprises a combined dosage of umeclidinium bromide and vilanterol trifenatate. In certain embodiments, the combined dosage of umeclidinium bromide and vilanterol trifenatate is delivered by any one of the following methods: aerosol, nebulized, powder, metered, and inhalation. In certain embodiments, the combined dosage of umeclidinium bromide and vilanterol trifenatate is delivered via inhalation. In certain embodiments, the medicament comprises a combined dosage of fluticasone furoate and vilanterol trifenatate. In certain embodiments, the combined dosage of fluticasone furoate and vilanterol trifenatate is delivered by any one of the following methods: aerosol, nebulized, powder, metered, and inhalation. In certain embodiments, the combined dosage of fluticasone furoate and vilanterol trifenatate is delivered via inhalation. In certain embodiments, the combined dosage of fluticasone furoate and vilanterol trifenatate contains any one of 0.030, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, and 0.3 mg of fluticasone furoate. In certain embodiments, the combined dosage of fluticasone furoate and vilanterol trifenatate contains any one of 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, and 0.050 mg vilanterol trifenatate.

In one aspect, the subject has been exposed to a virus that increases the likelihood or severity of respiratory damage. In one aspect, the subject has been exposed to a virus that increases the likelihood or severity of lung damage. In one aspect, the subject has a genetic predisposition to develop lung fibrosis.

In certain embodiments, the subject has been exposed to a coronavirus ("CoV"). In certain embodiments, the subject has been exposed to a severe acute respiratory syndrome coronavirus ("SARS-CoV"). In certain embodiments, the subject has been exposed to the severe acute respiratory syndrome coronavirus 2 ("SARS-CoV-2").

In one aspect, the exposure of the subject to the virus is established by the proximity of the subject with a known carrier of the virus. In one aspect, the exposure of the subject to the virus is established by the proximity of the subject with a known carrier of the virus for a period of time.

In one aspect, the exposure of the subject to the virus is confirmed by a positive titer for the virus. In another aspect, the exposure of the subject to the virus is confirmed by a positive titer for antibodies to the virus. In yet another aspect, the exposure of the subject to the virus is confirmed by recognized clinical symptoms associated with the virus.

In certain embodiments, the subject has been exposed to SARS-CoV-2, and the exposure of the subject to the SARS-CoV-2 virus is confirmed by one or more recognized clinical symptoms associated with the SARS-CoV-2 virus. In certain further embodiments, the one or more recognized clinical symptoms associated with the SARS-CoV-2 virus include one or more of the following: fever, chills, shortness of breath, dyspnea, tremors, fatigue, myalgia, headache, taste dysfunction, and smell dysfunction. In a further aspect, the subject has experienced depressed pulmonary activity. The depressed pulmonary activity may be manifested by a decreased blood oxygenation level, the need for administering supplemental oxygen, or the need for a respirator.

In some aspects of the present disclosure, after treatment, the subject experiences a substantial reduction in the rate of pulmonary fibrosis progression compared to pre-treatment. This reduction can be quantified by objective measures (chest X-ray, pulmonary function tests, etc.).

In some aspects of the present disclosure, after treatment, the subject experiences a substantial reduction in the hospitalization rate based on improved breathlessness, dyspnea, or cough status. In some embodiments, after the treatment, the patient experiences a substantial reduction of cough characterized by at least a one-point reduction in the cough severity Numerical Rating Scale (NRS) value compared to before treatment. In some embodiments, the reduction of cough is characterized by a decline in NRS cough value ranging from about 1.0 to about 9.0 points, for example, about 1.0 point, about 2.0 point, about 3.0 points, about 4.0 points, about 5.0 points, about 6.0 points, about 7.0 points, about 8.0 points, about 9.0 points and about 10.0 points compared to before treatment.

In some aspects of the present disclosure, after treatment, the subject experiences a substantial improvement in health status related to a reduction in cough frequency characterized by at least about a 1.0-point improvement in the total score on the patient's Leicester Cough Questionnaire (LCQ) score compared to before treatment. In some embodiments, the improvement in health status related to a reduction of cough frequency is characterized by an improvement in Leicester Cough Questionnaire score ranging from about 0.5 to about 2.0 points, for example, about 0.5 points, about 1.0 point, about 1.5 points, and about 2.0 points compared to before treatment. In some embodiments, the improvement in health status related to the reduction of cough frequency is characterized by an improvement in any of the three Leicester Cough Questionnaire domains (physical, psychological or social) score ranging from about 0.5 to about 2.0 points, for example, about 0.5 points, about 1.0 point, about 1.5 points, and about 2.0 points compared to before treatment.

In some aspects of the present disclosure, after the treatment, the subject experiences a substantial reduction of fatigue compared to before treatment. In some embodiments, after said treatment, the patient experiences a reduction of fatigue characterized by at least one category change in at least one of the 7 questions of the PROMIS Item Bank v1.0 Fatigue Short Form 7a Scale. In some embodiments, the reduction of fatigue is characterized by an improvement in at least one of the 7 questions of the PROMIS Item Bank v1.0 Fatigue Short Form 7a Scale ranging from at least one category to about three categories, for example, about one category, about two categories, about three categories, about four categories, about five categories, about six categories, and about seven categories compared to before treatment.

In some aspects of the present disclosure, after the treatment, the subject experiences a substantial reduction in the frequency and/or severity of breathlessness episodes. In some embodiments, after treatment, the patient experiences a reduction of breathlessness characterized by at least a 1.0-point reduction in the Evaluating Respiratory Symptoms (E-RS™) breathlessness subscale score compared to before treatment. In some embodiments, the reduction of breathlessness is characterized by a decline in Evaluating Respiratory Symptoms (E-RS™) breathlessness subscale score ranging from about 1.0 to about 23.0 points (Bacci E D, O'Quinn S, Leidy N K, Murray L, Vernon M. Evaluation of a respiratory symptom diary for clinical studies of idiopathic pulmonary fibrosis. Respir Med. 2018 January; 134:130-138), for example, about 1.0 point, about 3.0 points, about 5.0 points, about 7.0 points, about 9.0 points, about 11.0 points, about 13.0 points, about 15.0 points, about 17.0 points, about 19 points, about 21 points and about 23.0 points compared to before treatment.

In some aspects of the present disclosure, after the treatment, the subject experiences a substantial reduction in the frequency and/or severity of dyspnea episodes. In some embodiments, after said treatment, the patient experiences a reduction of dyspnea characterized by at least a one-point change in the Borg dyspnea scale value total score compared to before treatment. In some embodiments, the reduction of dyspnea is characterized by a decline in Borg dyspnea scale value total score ranging from about 0.5 to about 2.0 points, for example, about 0.5 points, about 1.0 point, about 1.5 points, and about 2.0 points compared to before treatment.

In some aspects of the present disclosure, after the treatment, the patient experiences a substantial reduction in the hospitalization rate based on improvement in breathlessness, dyspnea, or cough status.

Abbreviations and Definitions

To aid understanding of the disclosure, many terms and abbreviations as used herein are defined below as follows:

When introducing elements of the present disclosure or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "and/or" when used in a list of two or more items means that any one of the listed items can be employed by itself or in combination with any one or more of the listed items. For example, the expression "A and/or B" is intended to mean either or both of A and B, i.e., A alone, B alone, or A and B in combination. The expression "A, B, and/or C" is intended to mean A alone, B alone, C alone, A and B in combination, A and C in combination, B and C in combination, or A, B, and C in combination.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein in relation to a numerical value x means x±10%.

The term "disease" as used herein is intended to be generally synonymous and is used interchangeably with the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means administering two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. Also, such administration encompasses the use of each type of therapeutic agent in a sequential manner. In either case, the treatment regimen will benefit the drug combination in treating the conditions or disorders described herein.

The phrase "therapeutically effective" or "effective amount" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of subjects without undue toxicity, irritation, and allergic response, are commensurate with a reasonable benefit/risk ratio and are effective for their intended use.

Reference to "treatment" of a subject is intended to include prevention, prophylaxis, attenuation, amelioration, and therapy. Treatment may also include the prevention of disease. Prevention of a disease may involve complete protection from disease, such as preventing infection with a pathogen or may involve prevention of disease progression.

For example, prevention of a disease may not mean complete foreclosure of any effect related to the diseases at any level. Instead, it may mean preventing the symptoms of a disease to a clinically significant or detectable level. The prevention of diseases may also mean preventing disease progression to a later stage of the disease.

The terms "subject" or "patient" are used interchangeably herein to mean all mammals, including humans. In certain embodiments, the subject is a human. In certain embodiments, the subject is a human or mammal. In certain embodiments, the subject is chosen from a human and mammal. Examples of subjects include, but are not limited to, humans, monkeys, dogs, cats, horses, cows, goats, sheep, pigs, and rabbits.

The terms "affected with a disease or disorder," "afflicted with a disease or disorder," or "having a disease or disorder" are used interchangeably herein and refer to a subject with any disease, disorder, syndrome, or condition. One of the terms implies no increased or decreased level of severity of the disorder compared to the other.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in preparing and purifying the compound in question. Basic addition salts may also be formed and be pharmaceutically acceptable. For a complete discussion of the preparation and selection of salts, refer to Pharmaceutical Salts: Properties, Selection, and Use (Stahl, P. Heinrich. Wiley-VCHA, Zurich, Switzerland, 2002).

The term "pulmonary disease" refers to diseases affecting the organs involved in breathing, including but not limited to the nose, throat, larynx, Eustachian tubes, trachea, bronchi, lungs, related muscles, and nerves. Pulmonary diseases include, but are not limited to, asthma, adult respiratory distress syndrome, and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "sequela" (plural "sequelae") refers to a disease or symptoms that affect a subject as a consequence of the subject has experienced a disease, infection, illness, or injury. In some aspects, a sequela is diagnosed no earlier than 1, 2, 3, 6, 12, 18, or 24 months after the disease, infection, illness, or injury. In some aspects, a sequela is diagnosed no later than 6, 12, 18, 24, or 30 months after the disease, infection, illness, or injury.

The terms "fibrosis" and "fibrosing disorder" refer to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to lung diseases associated with fibrosis, including but not limited to idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); chronic nephropathies associated with injury/fibrosis (kidney fibrosis), including but not limited to glomerulonephritis secondary to systemic inflammatory diseases such as lupus and scleroderma, diabetes, glomerular nephritis, focal segmental glomerular sclerosis, IgA nephropathy, hypertension, allograft and Alport syndrome; gut fibrosis, including but not limited to scleroderma, and radiation induced gut fibrosis; liver fibrosis, including but not limited to cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; head and neck fibrosis, e.g., radiation induced; corneal scarring, e.g., LASIK (laser-assisted in situ keratomileusis), corneal transplant, and trabeculectomy; hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

The term "therapeutically acceptable salt" represents salts or zwitterionic forms of the compounds disclosed herein, which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids that can be employed to form therapeutically acceptable addition salts include inorganic acids such as hydrochloric, hydrobromic, sulfuric, phosphoric, and organic acids such as oxalic, maleic, succinic, and citric. Salts can also be formed by coordinating the compounds with an alkali metal or alkaline earth ion. Hence, the present disclosure contemplates sodium, potassium, magnesium, and calcium salts of the compounds disclosed herein and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for forming base addition salts include ethylenediamine, ethanolamine, diethanolamine, piperidine, and piperazine.

A salt of a compound can be made by reacting the appropriate compound as the free base with the appropriate acid.

Pharmaceutical Formulations

While it may be possible for the compounds disclosed herein to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and understood in the art, e.g., in Remington's Pharmaceutical Sciences. The pharmaceutical compositions disclosed herein may be manufactured in any manner known in the art, e.g., through conventional mixing, dissolving, granulating, dragee-making, levigating, emulsifying, encapsulating, entrapping, or compression processes.

The formulations include those suitable for oral, parenteral (including subcutaneous, intradermal, intramuscular, intravenous, intraarticular, and intramedullary), intraperitoneal, transmucosal, transdermal, rectal, and topical (including dermal, buccal, sublingual, and intraocular) administration. However, the most suitable route may depend upon, for example, the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug, or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Fillers include, but are not limited to, lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dihydrate. In one embodiment, the filler is not water-soluble, although it may absorb water. In one embodiment, the filler is a spheronization aid. Spheronization aids can include one or more crospovidone, carrageenan, chitosan, pectinic acid, glycerides, β-cyclodextrin (β-CD), cellulose derivatives, microcrystalline cellulose, powdered cellulose, polyplasdone crospovidone, and polyethylene oxide.

Binders include, but are not limited to, cellulose ethers, methylcellulose, ethylcellulose, hydroxyethylcellulose, propyl cellulose, hydroxypropyl cellulose, lower-substituted hydroxypropyl cellulose, hydroxypropylmethylcellulose (hypromellose, e.g., hypromellose 2910, Methocel™ E), carboxymethyl cellulose, starch, pregelatinized starch, acacia, tragacanth, gelatin, polyvinyl pyrrolidone (povidone), cross-linked polyvinyl pyrrolidone, sodium alginate, microcrystalline cellulose, and lower-alkyl-substituted hydroxypropyl cellulose. In one embodiment, the binders are selected from wet binders.

Surfactants include, but are not limited to, anionic surfactants, including sodium lauryl sulfate, sodium deoxycholate, dioctyl sodium sulfosuccinate, and sodium stearyl fumarate, nonionic surfactants, including polyoxyethylene ethers and polysorbate 80, and cationic surfactants, including quaternary ammonium compounds. In one embodiment, the surfactant is selected from anionic surfactants, e.g., sodium lauryl sulfate.

Disintegrants include, but are not limited to, starch, sodium cross-linked carboxymethyl cellulose, carmellose sodium, carmellose calcium, cross-linked polyvinyl pyrrolidone, and sodium starch glycolate, low-substituted hydroxypropyl cellulose, and hydroxypropyl starch.

Glidants include, but are not limited to, polyethylene glycols of various molecular weights, magnesium stearate, calcium stearate, calcium silicate, fumed silicon dioxide, magnesium carbonate, magnesium lauryl sulfate, aluminum stearate, stearic acid, palmitic acid, cetanol, stearol, and talc.

Lubricants include, but are not limited to, stearic acid, magnesium stearate, calcium stearate, aluminum stearate, and siliconized talc In certain embodiments, the formulation further comprises one or more antioxidants. Examples of pharmaceutically-acceptable antioxidants include (1) water-soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediaminetetraacetic acid (EDTA), sorbitol, tartaric acid, phosphoric acid, and the like.

Routes of Administration

Oral Administration

The compounds of the present disclosure may be administered orally, including swallowing, so the compound enters the gastrointestinal tract or is absorbed into the bloodstream directly from the mouth, including sublingual or buccal administration.

Suitable compositions for oral administration include solid formulations such as tablets, pills, cachets, lozenges, and hard or soft capsules, containing liquids, gels, powders, or granules.

In a tablet or capsule dosage form, the amount of drug present may be from about 0.05% to about 95% by weight, more typically from about 2% to about 50% by weight of the dosage form.

Also, tablets or capsules may contain a disintegrant, comprising from about 0.5% to about 35% by weight, more typically from about 2% to about 25% of the dosage form. Examples of disintegrants include methylcellulose, sodium or calcium carboxymethyl cellulose, croscarmellose sodium, polyvinylpyrrolidone, hydroxypropyl cellulose, starch, and the like.

Suitable binders for use in a tablet include gelatin, polyethylene glycol, sugars, gums, starch, hydroxypropyl cellulose, and the like. Suitable diluents for use in a tablet include mannitol, xylitol, lactose, dextrose, sucrose, sorbitol, and starch.

Suitable surface-active agents and glidants for use in a tablet or capsule may be present in amounts from about 0.1% to about 3% by weight and include polysorbate 80, sodium dodecyl sulfate, talc, and silicon dioxide.

Suitable lubricants for use in a tablet or capsule may be present in amounts from about 0.1% to about 5% by weight and include calcium, zinc or magnesium stearate, sodium stearyl fumarate, and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, lubricating, surface active, or dispersing agents. Molded tablets may be made by molding a mixture of the powdered compound moistened with a liquid diluent in a suitable machine. Dyes or pigments may be added to tablets to identify or characterize different combinations of active compound doses.

Liquid formulations can include emulsions, solutions, syrups, elixirs, and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as an immediate or modified release, including delayed or sustained release, optionally with enteric coating.

In another embodiment, a pharmaceutical composition comprises a therapeutically effective amount of a compound of Formula (I) or a pharmaceutically acceptable salt thereof and a pharmaceutically acceptable carrier.

Parenteral Administration

Compounds of the present disclosure may be administered directly into the bloodstream, muscle, or internal organs by injection, e.g., by bolus injection or continuous infusion. Suitable means for parenteral administration include intravenous, intramuscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example, sealed ampoules and vials.

Most parenteral formulations are aqueous solutions containing excipients, including salts, buffering, suspending, stabilizing, and/or dispersing agents, antioxidants, bacteriostats, preservatives, and solutes which render the formulation isotonic with the blood of the intended recipient and carbohydrates.

Parenteral formulations may also be prepared in a dehydrated form (e.g., by lyophilization) or sterile non-aqueous solutions. These formulations can be used with a suitable vehicle, such as sterile water. Solubility-enhancing agents may also be used for preparing parenteral solutions.

Compositions for parenteral administration may be formulated as an immediate or modified release, including delayed or sustained release. Compounds may also be formulated as depot preparations. Such long-acting formulations may be administered by implantation (for example, subcutaneously or intramuscularly) or intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Methods of Delivery

This disclosure contemplates the following modes of delivery:

PEG (polyethylene glycol (PEG) or PEGylated, or particulate form as used and defined nicotine or cannabis electronic cigarettes (e-cig or vaping), including but not limited to salts of the therapeutic components such as protonated forms of the therapeutics disclosed containing the pharmacologic agent of interested taken from any dose or combination of corticosteroid, beta2 adrenoreceptor agonist and tyrosine kinase antagonist listed above, in this disclosure.

Soft Mist inhaler, nebulizer, HFA (hydrofluoroalkane metered-dose inhaler with or without a spacer, Vaping device consisting of an atomizer, a power source such as a self-contained battery, and a container such as a cartridge or a tank, whereby instead of the user inhaling smoke, the user inhales a vapor form of the therapeutic and delivery vehicle contained or administered within said container.

A salt liquid formulation containing the pharmacologic agent of interest taken from any dose or combination of corticosteroid, beta2 adrenoreceptor agonist, and tyrosine kinase antagonist listed above, in this disclosure, for generating an inhalable aerosol in an electronic cigarette comprising a salt that forms about 0.5% to about 50% pharmacologic agent is provided. Provided herein is a method of delivering the pharmacologic agent to a user comprising operating an electronic cigarette to a user wherein the electronic cigarette comprises a salt of the pharmacologic agent formulation comprising a pharmacologic agent salt in a biologically acceptable liquid carrier wherein an acid used to form said pharmacologic agent salt is characterized by vapor pressure >20 mmHg at 200° C., and inhaling an aerosol generated from the pharmacologic agent salt formulation heated by the electronic cigarette.

A method of delivering a pharmacologic "agent" consisting of any dose of any combination of corticosteroid, beta2 adrenoreceptor agonist and tyrosine kinase antagonist listed above, in this disclosure, to a user comprising deploying an electronic cigarette comprising a formulation comprising said "agent" in a biologically acceptable liquid carrier, wherein the operation of the electronic cigarette generates an inhalable aerosol.

An aspect of the present invention relates to a substantially pure conjugate containing one or more polymer moieties, a protein moiety, and a linker to the pharmacologic agent of interest taken from any dose or combination of corticosteroid beta2 adrenoreceptor agonist and tyrosine kinase antagonist listed above, in this disclosure. In the conjugate, the polymer moiety or moieties are attached to the linker; the nitrogen atom of the N-terminus of the pharmacologic moiety is bonded to the linker; the linker is a covalent bond, C1-10 alkylene, C2-10 alkenylene, or C2-10 alkynylene; and the pharmacologic moiety consists of any combination of corticosteroid, beta2 adrenoreceptor agonist and tyrosine kinase antagonist listed above, in this disclosure. This conjugate has an unexpected long in vivo half-life.

Topical Administration

Compounds of the present disclosure may be administered topically (for example, to the skin, mucous membranes, ear, nose, or eye) or transdermally. Formulations for topical administration can include, but are not limited to, lotions, solutions, creams, gels, hydrogels, ointments, foams, implants, patches, and the like. Carriers that are pharmaceutically acceptable for topical administration formulations can include water, alcohol, mineral oil, glycerin, polyethylene glycol, and the like. Topical administration can also be performed by, for example, electroporation, iontophoresis, phonophoresis, and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as an immediate or modified release, including delayed or sustained release.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated conventionally. Such compositions may comprise the active ingredient in a flavored basis, such as sucrose and acacia or tragacanth.

Administration by Inhalation

For administration by inhalation, compounds may be conveniently delivered from an insufflator, nebulizer pressurized packs, or other convenient means of delivering an aerosol spray or powder. Pressurized packs may comprise a suitable propellant such as dichlorodifluoromethane, trichlorofluoromethane, dichlorotetrafluoroethane, carbon dioxide, or other suitable gas. In a pressurized aerosol, the dosage unit may be determined by providing a valve to deliver a metered amount. Alternatively, for administration by inhalation or insufflation, the compounds according to the disclosure may take the form of dry powder composition, for example, a powder mix of the compound and a suitable powder base such as lactose or starch. The powder composition may be presented in a unit dosage form, such as capsules, cartridges, gelatin, or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Unit dosage formulations contain an effective dose, as herein recited, or an appropriate fraction thereof, of the active ingredient. The precise amount of compound administered to a subject will be the responsibility of the attendant physician. The specific dose level for any particular subject will depend upon a variety of factors, including the activity of the specific compound employed, the age, body weight, general health, sex, diets, time of administration, route of administration, rate of excretion, drug combination, the precise disorder being treated, and the severity of the indication or condition being treated. Also, the route of administration can and will vary depending on the condition and its severity. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Methods of Treatment

The methods of the disclosure can be used to treat any subject in need of treatment.

In various embodiments, the disclosed methods are used (1) to treat immediately (acutely) so that long term sequelae are reduced, (2) to treat continuously (maintenance therapy) for a fixed or defined time or for an extended and undefined time period, or (3) to treat symptomatically (as needed) after viral recovery. The severity of the disease has been correlated with the long-term outcomes, regardless of the SARS2 variant.

Examples of subjects include, but are not limited to, humans, monkeys, deer, camel, pets, and companion animals, including, but not limited to, dogs, cats, horses, rabbits, and guinea pigs; livestock, including, but not limited to, cows, buffalo, bison, mules, goats, sheep, and pigs. In one embodiment, the subject is a human.

Asthma

In certain embodiments, the methods disclosed herein are used to treat asthma in a subject which is a consequence of previous exposure of the subject to a virus, particularly SARS-CoV-2. The inflammation associated with asthma represents exaggerated repair processes which can, themselves, lead to airway damage.

In one aspect, in the asthmatic individual, the release of normal repair mediators, including lysophosphatidic acid (LPA), is exaggerated. The actions of the repair mediators are inappropriately prolonged, leading to airway damage. In some aspects, the airway damage associated with asthma may include a thickened lamina reticularis, increased count and activity of myofibroblasts, increased numbers and secretory activity of mucus glands, thickening of the smooth muscle layer, and altered morphology of both the connective tissue and capillary bed throughout the airway wall. Thickening of the airway wall can, in turn, constrict the lumen of the asthmatic airway, thus decreasing airflow.

Fibrosis

In certain embodiments, the methods disclosed herein are used to treat fibrosis in a subject, resulting from previous exposure of the subject to a virus, particularly SARS-CoV-2. Tissue injury initiates a complex series of host wound-healing responses. Failure of these responses, which otherwise would restore normal tissue structure and function, can lead to tissue fibrosis and loss of function. Several events and factors play roles in developing fibrosis in organs, including without limitation the lungs. Molecules involved in fibrosis development include proteins or peptides, such as cytokines, chemokines, metalloproteinases, and phospholipids.

In the lung, failure of the wound healing responses can contribute to the pathogenesis of fibrotic lung diseases. Fibrotic lung diseases, such as idiopathic pulmonary fibrosis (IPF), are associated with high morbidity and mortality.

Fibrosis can also manifest in related respiratory ailments. Peribronchiolar fibrosis can lead to chronic bronchitis, emphysema, and interstitial lung disease. Fibrosis of the alveolar wall is associated with emphysema. Other manifestations of fibrosis include fibrotic interstitial lung diseases and obliterative bronchiolitis, and chronic obstructive pulmonary disease.

Pulmonary fibrosis involves the hardening and scarring of lung tissue due to excess deposition of extracellular matrix components, including collagen, by fibroblasts. Fibroblasts participate in inflammation and immune cell recruitment to sites of tissue injury, and both produce and can respond to inflammatory cytokines.

The diagnosis of pulmonary fibrosis can usually be made by a careful history, including physical examination, chest radiography, including a high-resolution computer tomographic scan (HRCT), and open lung or transbronchial biopsies. Histologic examination of tissue obtained at open lung biopsy allows classification of these patients into several categories, including Usual Interstitial Pneumonia (UIP), Desquamative Interstitial Pneumonia (DIP), and Non-Specific Interstitial Pneumonia (NSIP).

In one aspect, a method of the present disclosure comprises the administration of a compound as disclosed herein or a pharmaceutically acceptable salt to a subject. In one aspect, the aforementioned method is directed at treating fibrosis of an organ or tissue in a subject, preferentially the lungs or pulmonary tissue. One aspect is a method for preventing a fibrosis condition in a subject. The method comprises administering to the subject at risk of developing one or more fibrosis conditions a therapeutically effective amount of a compound as disclosed herein or a pharmaceutically acceptable salt thereof.

Combinations and Combination Therapy

The compounds of the present disclosure can be used, alone or in combination with other pharmaceutically active compounds, to treat conditions such as those disclosed hereinabove. The compound(s) of the present disclosure and other pharmaceutically active compound(s) can be administered simultaneously (either in the same dosage form or in separate dosage forms) or sequentially. Accordingly, in one embodiment, the present disclosure comprises methods for treating a condition by administering to the subject a therapeutically-effective amount of one or more compounds of the present disclosure and one or more additional pharmaceutically active compounds.

In some embodiments, the method of the current disclosure includes the coadministration of at least one antitussive, anti-breathlessness, and anti-dyspneic drug.

In some embodiments, the method of the current disclosure includes the coadministration to the subject with fibrosis, or with a predisposition of developing fibrosis, with one or more other agents that are used to treat fibrosis. In one aspect, the one or more agents include corticosteroids. In one aspect, the one or more agents include immunosuppressants. In one aspect, the one or more agents include B-cell antagonists. In one aspect, the one or more agents include uteroglobin.

In another embodiment, there is provided a pharmaceutical composition comprising one or more compounds of the present disclosure, one or more additional pharmaceutically active compounds, and a pharmaceutically acceptable carrier.

The methods disclosed herein can also include coadministration with other therapeutic reagents selected for their therapeutic value for the condition to be treated. In general, the compounds described herein and, in embodiments where combination therapy is employed, other agents do not have to be administered in the same pharmaceutical composition. Because of different physical and chemical characteristics, they are optionally administered by different routes. The initial administration is generally made according to established protocols and then, based upon the observed effects, the dosage, modes of administration, and times of administration subsequently modified. The subject's overall benefit is either simply additive of the two therapeutic agents, or the subject experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically-effective dosages of drugs and other agents for use in combination treatment regimens are documented methodologies. Combination treatment further includes periodic treatments that start and stop at various times to assist with the clinical management of the subject. In any case, the multiple therapeutic may be administered in any order or simultaneously. If simultaneously, the multiple therapeutic agents are optionally provided in a single, unified form, or multiple forms (by way of example only, either as a single pill or as two separate pills).

In some embodiments, one of the therapeutic agents is given in multiple doses, or both are given multiple doses. If not simultaneous, the timing between the multiple doses optionally varies from more than zero weeks to less than twelve weeks.

Also, the combination methods, compositions, and formulations are not limited to the use of only two agents. The use of multiple therapeutic combinations is also envisioned. It is understood that the dosage regimen to treat, prevent, or ameliorate the condition(s) for which relief is sought is optionally modified per various factors. These factors include the disorder from which the subject suffers and the subject's age, weight, sex, diet, and medical condition. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life, and kinetic profile of the pharmaceutical agent.

Where a subject is suffering from or at risk of suffering from an inflammatory condition, the methods as disclosed herein may include the coadministration of one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDEVIMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

Biological and Clinical Assays

The following are examples of biological and clinical assays useful with the methods of the disclosure. The assays provided herein are not limiting, and other assays are now known, or later discovered, by one of skill in the art can be used for the same purpose as the assays provided below.

Intratracheal inoculation of bleomycin Eight to ten-week-old male C57BL/6 mice weighing 24 to 28 g are used for the experiments. After measuring their body weight, the mice are anesthetized with an intraperitoneal injection of avertin. The mice's trachea is exposed by a 1.0 cm longitudinal incision in the neck and injected with 55 µL of a bleomycin hydrochloride solution containing 1.5 mg or 2.0 mg of bleomycin dissolved in a sterile phosphate-buffered saline solution per kilogram of body weight. The test mice are treated with 50 µg alloferon intraperitoneally daily from the day of bleomycin inoculation. All procedures are conducted in a sterile environment and are reviewed and approved by the appropriate Institutional Review Board.

Histopathological scoring Mice are euthanized with $CO_2$ asphyxiation. After thoracotomy, the lungs are perfused with saline via the right ventricle and inflated with 2 mL of phosphate-buffered 4% paraformaldehyde solution via the trachea and fixed for 24 hours. Routine light microscopic techniques are performed for paraffin embedding, and the sections are stained with H&E and Masson's trichrome.

Bronchoalveolar (BAL) cell counting Mice are sacrificed by asphyxiation in a $CO_2$ chamber. The mice are dampened with 70% ethanol in a biosafety cabinet. The mice are then placed front side up on a Styrofoam panel, and the arms and legs of the mice are fixed with needles or tape. Scissors are used to make an incision in the skin from the abdomen to the neck, and the skin retracted with forceps to expose the thoracic cage and neck. The muscle around the neck is gently removed to expose the trachea. Forceps are used to put an approximately 10 cm-long nylon string under the trachea. The ribs are then cut to expose the heart and the lungs without cutting the trachea and lungs. A 22G×1 in. Exel Safelet Catheter is inserted into the trachea, the stylet hub removed, and the catheter and the trachea are tied together firmly with the nylon string.

A 1-mL syringe is loaded with 0.8 ml of phosphate-buffered saline (PBS) and placed at the end of the catheter. The PBS is injected and aspirated four times. The syringe is then removed from the catheter, and the recovered lavage fluid is saved in 1.5 mL Eppendorf tubes on ice. The BAL volume is recorded according to the scales on the 1.5 mL Eppendorf tubes. The BAL fluid is centrifuged at 800 g for 10 min at 4° C. After centrifugation, the supernatant is transferred to a new 5 ml tube, with a protease inhibitor cocktail added to a final concentration of 1× and PMSF to a final concentration of 1 mM and mixed well. The BAL cell pellets are resuspended in 400 µL of PBS, and the cells are counted by taking about 20 µL of the cell sample to a hemocytometer and counting the cells under a microscope.

Collagen content measurement Lung tissue is homogenized in 100 µL ddH2O. To a 100 µL of sample homogenate, 100 µL concentrated HCl C12 M) is added in a pressure-tight Teflon capped vial. The samples are hydrolyzed at 120° C. for 3 hrs. After homogenization, the samples are clarified by adding 4 mg of activated charcoal. The samples are then vortexed and centrifuged at 10,000 g for 3 min to remove the precipitate and activated charcoal. 10-30 µL of each hydrolyzed sample is transferred to a 96-well plate and evaporated to dryness under vacuum/on a hot plate/in an oven. A 1.0 mg/ml Collagen I Standard is prepared by adding 50 µL of 2 mg/mL Type I Standard to 50 µL of 0.02 M AcOH and generating 0, 2, 4, 6, 8, and 10 µg of collagen/well. The volume is adjusted to 10 µ/vial with 0.02 M AcOH. 10 µL of 12 M HCl is then added to the pressure-tight Teflon capped vial and hydrolyzed at 120° C. for 3 hrs. The vials are placed on ice, and the contents are spun down. Each vial's contents are transferred to a 96-well plate and evaporated to dryness under vacuum/on a hot plate/in an oven. 100 µL of Chloramine T reagent is added to each sample and standard and incubated at room temperature for 5 min. 100 µL of the DMAB reagent is then added to each well and incubated for 90 min. at 60° C. Absorbance is measured at 560 nm in a microplate reader. Total collagen concentration (C) is calculated as follows (C)=B/V×D µg/µL (B; amount of collagen in the sample well from Standard Curve (µg), V; sample volume added into the reaction well (µL), D: sample dilution factor).

Cough reduction Reduction of cough in subjects treated with the methods of the current disclosure can be determined by various methods. In some embodiments, the effectiveness of a dosage regimen can be determined by evaluation via a cough severity Numerical Rating Scale (NRS) test value, a Leicester Cough Questionnaire score, daytime cough frequency measured using cough count monitor device, 24-hour cough frequency measured using cough count monitor device, night-time cough frequency measured using cough count monitor device, cough quality of life questionnaire (CQLQ©) total value, Clinical Global Impression of Change (CGIC), PROMIS Item Bank v1.0-Fatigue Short Form 7a scale, St. George's Questionnaire for the IPF population (SGRQ-I) total score, EXAcerbation of Chronic pulmonary disease Tool (EXACT®) version 1.1 e-diary tool total score, Evaluating Respiratory Symptoms, (E-RS™) daily diary (the E-RS™ is an 11 respiratory symptoms item derivative instrument of the EXACT® tool) cough subscale score, chest symptoms subscale score as well as the E-RS™ total score or any combination thereof. In some embodiments, the effectiveness of a dosage regimen can be determined by evaluation via a daytime cough frequency measured using a cough count monitor device as a primary efficacy endpoint in association with secondary efficacy endpoints such as a Leicester Cough Questionnaire score.

Breathlessness reduction Reduction of breathlessness or dyspnea (including in IPF patients) in subjects treated with the methods of the current disclosure can be determined by various methods. In some embodiments, the effectiveness of a dosage regimen can be determined by evaluation via an Evaluating Respiratory Symptoms (E-RS™) breathlessness subscale score (that includes an assessment of breathlessness with activity (dyspnea)), Borg dyspnea scale value total score, Borg dyspnea scale domains (sensory-perceptual, affective distress or symptom impact), numerical rating scale dyspnea value, Modified Medical Research Council Scale, PROMIS Pool v1.0 Dyspnea Emotional Response Scale, PROMIS Item Bank v1.0 Dyspnea Severity-Short Form 10a Scale, PROMIS Item Bank v1.0 Dyspnea Characteristics Scale or any combination thereof.

Patients demonstrated a wide range of decreases in pulmonary function testing using the measures as described below that included both obstructive as well restrictive diseases in nature, as well as demonstrated by clinical testing.

Obstructive exhalation from the lungs is impeded due to airway resistance, causing a decreased flow of air.

Restrictive lung tissue and/or chest muscles fail to expand sufficiently, impeding airflow, mostly due to lower lung volumes.

Pulmonary flow testing (PFTs) include spirometry and plethysmography

Spirometry pulmonary flow from a subject is measured with a spirometer, a device with a mouthpiece designed to measure airflow.

Plethysmography pulmonary flow from a subject is measured by positioning the subject in a plethysmograph: an air-tight chamber with the appearance of a short, square telephone booth that can measure inhalation and exhalation via changes in pressure.

Measurements that can be obtained from PFT studies include the following:

Tidal volume (VT) the amount of air inhaled or exhaled during normal breathing.

Minute volume (MV) the total amount of air exhaled per minute.

Vital capacity (VC) the total air volume that can be exhaled after inhalation with maximum effort.

Functional residual capacity (FRC) the amount of air left in the lungs after exhaling normally.

Residual volume the amount of air left in the lungs after exhalation with maximum effort.

Total lung capacity the total volume of the lungs upon inhalation with maximum effort.

Forced vital capacity (FVC) the amount of air exhaled forcefully and quickly after inhalation with maximum effort.

Forced expiratory volume (FEV) the amount of air that expired during the first, second, and third seconds of the FVC test.

Forced expiratory flow (FEF) the average flow rate during the middle half of the FVC test.

Peak expiratory flow rate (PEFR) the fastest achievable rate of exhalation.

Lung diffusion capacity a test, similar to spirometry, for measuring how well oxygen moves from the patient's lungs into the patient's blood. The test can help diagnose a disease of the blood vessels between the patient's heart and lungs. It can show the amount of damage done by a disease such as emphysema, a disease in which the patient's air sacs (alveoli) are gradually destroyed.

Bronchial provocation test Triggers such as exercise, smoke, and dust can initiate labored breathing in asthmatics. A bronchial provocation test can help diagnose asthma and estimate the severity of the condition. To perform the test, the subject inhales a medication that narrows airways, after which a spirometry measurement is performed several times. Interpretation of these measurements by a doctor can indicate how airways narrow during an asthma attack.

Cardiopulmonary exercise stress test This test, generally given to subjects who may have heart disease or lung problems (which may present only during exercise), measures lung and heart strength. To perform the test, the subject walks on a treadmill or rides a stationary bicycle. During this period, both the heart rate and lung performance are monitored. Interpretation of these measurements by a doctor can indicate the presence and/or severity of heart disease or lung problems.

Pulse oximetry test This painless test measures the oxygen content in the bloodstream. A probe is clipped to the subject's finger, earlobe, or another part of the skin. The probe uses light to measure the level of oxygen in red blood cells.

Arterial blood gas test This test measures the levels of gases such as oxygen and carbon dioxide in arterial blood. A nurse or technician withdraws blood, probably from the wrist of the subject.

Fractional exhaled nitric oxide test Certain variants of asthma present with elevated levels of nitric oxide (NO) in the body. The fractional exhaled nitric oxide test measures the NO content in exhaled air.

Body plethysmography Measures the volume of air that can be held in the lungs of a subject. The test is performed in a small, airtight room while the subject breathes against a mouthpiece.

DLCO (diffusing capacity of the lung for carbon monoxide) test Assesses how well lungs exchange gases. During the test you will inhale air containing a small amount of gas (e.g., carbon monoxide), hold your breath, then quickly breathe out. The amount of gas absorbed during the breath is measured through the gas exhaled.

Maximum inspiratory/expiratory pressures Determines respiratory muscle weakness by measuring the amount of pressure applied by the inspiratory and expiratory muscles.

Helium dilution FRC (functional residual capacity) determination This technique measures all the air in the lung that goes through gas exchange. Wearing nose clips, the subject breathes normally into a mouthpiece and then slowly exhales to empty the lungs. After repeating this a few times, you'll rest for five to ten minutes and then repeat.

Shunt Qualification

High altitude simulation testing Used for people with lung disease who are planning to travel via airplane. It helps determine if extra oxygen is needed while flying at high altitudes.

Bronchial provocation test Spirometry is used before and after inhalation of a breathing spray (e.g., methacholine) to assess the sensitivity of the airways in the lungs.

Arterial Blood Gases and Arterial Line Placement

Bronchodilator Evaluations

Sputum induction for microbiological analysis Helps create extra moisture in the airways in the lungs so patients can cough up secretions more easily. They are generally performed in a negative pressure space.

Pulmonary exercise tests allow the physician to evaluate lungs and heart under conditions of increased metabolic demand.

These decreases in pulmonary function as measured by the previous tests in different subsets of the population were also revealed in pulmonary exercise tests, including:

Six-minute walks Simple patient-paced test to assess functional capacity.

Rest and exercise test: Mild treadmill exercise at selected speeds to determine patient's oxygen needs with everyday exertion.

Incremental exercise test: Treadmill speed is increased in small increments to determine a patient's maximal exercise capacity while monitoring inspired and expired $CO_2$ and $O_2$ gases.

As mentioned above in the above disclosure, SARS2 patients demonstrated both isolated changes in specific components of these PFT and pulmonary function tests and some patients across all aspects.

Patients demonstrate different patterns in changes in said measures over these time courses, including a wide range of continuous numerical values in the slope of these objective pulmonary measures described above, over time, of which some could be categorized as:
  1. a relative decrease in change over time, categorized by a negative slope or a "decrease."
  2. a relative increase in change over time, categorized by a slope near zero or a "plateau."
  3. a relative increase in change over time, categorized by a slope near zero or a "decrease."

Further, these patterns in slope could also be classified by the phase of the slopes as being generally:
  1. monophasic
  2. biphasic
  3. triphasic
  4. complex For example, a negative slope or decrease in structural changes seen on imaging would correspond to changes in structural lung changes on imaging markedly, slowly or gradually resolving, or decreasing, or improving or lessened over time). Conversely, a negative slope or decrease in physiological or functional changes as measured using testing measures described above would gradually or markedly correspond to physiological and functional changes or markedly worsening, or pulmonary function or capacity decreasing or deteriorating over time). While these structural and physiological/functional changes generally tracked each other in an inverse manner, meaning, for example, that a decrease slope pattern in structural lung change would correlate with an increase slope pattern in pulmonary function testing or exercise testing over time (said structural and physiological/functional changes evident usually within 0.3 to 3 months of one another) and vice versa, there were a significant number (>23%) of cases in which no such relationship was observed (for a decrease slope pattern in imaging, showing improving or resolving pulmonary structural changes, however, no corresponding change, improvement, and/or increased slope pattern in PFTs or exercise testing, and vice versa for functional and imaging changes) and even, in a minority of cases (<15%) such changes were contradictory (meaning pulmonary changes for example, where there were improvements in structural changes (decrease slope pattern) but also decreased slope patterns on PFTs or exercise testing (i.e. improved structural changes but actual worsening in pulmonary functional/physiological measures, and vice versa for physiological and structural). Similarly, such findings of "consistency" and "inconsistency" were also generally observed across these phase patterns.

Further, post-SARS2 patients demonstrated these aforementioned decreases in pulmonary structure and function using said measures and further. Such changes included decreases in overall pulmonary function, pulmonary or lung reserve, and/or capacity using said tests and measures described equating to a full continuous spectrum of decreases. For example, some patients exhibited objective, or equivalent losses of <10%, 10-20%, 20-30%, 30-40%, >50%, etc. in pulmonary capacity or pulmonary reserve, and that these losses and their timing and slopes could also be described by these slope patterns and phase patterns described.

Further, counter to the current art, these changes were observed regardless of the clinical severity of their SARS2 infection. Specifically, even moderate, mild, and even clinical asymptomatic SARS2 infected patients (in addition to clinically severely infected SARS2 infected patients) all demonstrated these heretofore post-SARS2 infection pulmonary sequelae including, but not limited to the heretofore described losses in lung structure and function. Thus, all covid patients, irrespective of clinical severity, viral load, duration of viral infection or clinical symptoms, hospitalization course or absence of hospitalization, age, gender, prior comorbidities, or available treatments—all were susceptible to, and >15% of all SARS2 infected patients demonstrated these previously described losses in pulmonary function and/or structure.

TABLE 1

Summary of maximum viral RNA load per location and COVID-19 clinical severity

| Author | URT | LRT | Feces | Blood |
|---|---|---|---|---|
| | Maximum viral copies/mL [log 10] on the day after symptom onset | | | |
| Mild | | | | |
| Wölfel et al. [7] a | ~6.61 × 10$^8$ on Day 4 (6.66 × 10$^8$ in publ.) | ~2.69 × 10$^8$ on Day 6 (7.11 × 10$^8$ copies/ swab in publ.) | ~3.55 × 10$^7$ on Day 9 | ND |
| Zou [13] # | ~2.19 × 10 7 on Day 4 | ND | ND | ND |
| G. Lui et al. [20],* | 2.50 × 10$^6$ on Day 4 | ND | 7.94 × 10$^3$ on Day 7 | ND |
| Zheng et al. [12], a | ND | ~2.00 × 10$^7$ on Day 11 | ND | ND |
| Moderate-Severe | | | | |
| Wölfel et al. [7] a | ND | ND | ND | ND |
| Zou [13] a | ~1.32 × 10$^8$ on Day 5 | ND | ND | ND |
| G. Lui et al. [20],* | 4.60 × 10$^9$ on Day 8 | 3.45 × 10$^8$ on Day 11 | 2.76 × 10$^6$ on Day 18 | 1 × 10$^4$ on Day 3 |
| Zheng et al. [12] a | ND | ~1.82 × 10$^6$ on Day 4 | ND | ND |

LRT: Lower respiratory tract, ND: Not determined, URT: Upper respiratory tract;
*all subjects in this study received Lopinavir/Ritonavir;
publ.: Publication;
an estimated data as digitalized from the graph. Number in brackets refer to listing in the reference list at Table 4 of Weiss, A. et al., *Spatial and temporal dynamics of SARS-CoV-2 in COVID-19 patients: A systematic review and meta-analysis*, 58 EBIOMEDICINE 102916 (2020).

Example 1

Inhaled corticosteroid and Beta2 agonist therapy during the acute phase transition from primary viral-mediated pneumocyte and lung parenchymal damage phase to induced innate and/or adaptive immune-mediated pneumocyte and lung parenchymal damage phase mitigates loss in lung function and pulmonary structure due to SARS2. This transition period can be determined in any number of ways, including but not limited to laboratory, blood, serum, urine, fecal, sputum, bronchial lavage, imaging, genomic, or tissue-based testing. This transition typically occurs clinically around 6-14 days from symptom onset, and in some instances can be demarcated in shifts to elevated levels of, or an increased slope in certain blood factors such as LDH, ferritin, complement, and C-reactive protein, or increasing degree or distribution of lung opacities consolidation, edema, lymphatic prominence, interstitial thickening, pulmonary emboli, pulmonary hypertension, large and medium-size vessel wall thickening or inflammation, and cardiac inflammation or enlargement, or heart failure. During this period, pharmacologic agents and combinations as disclosed herein can be administered as a means to limit, contain, or restrain inflammatory/immune mediated damage and limit the progression of SARS2 associated lung damage as described above both physiologically functionally and structurally. This drug can be administered in asymptomatic, mild, moderate, and severe SARS2 disease patients. Ideally, within 4-7 days of this transition from primary viral-mediated lung damage to immune-mediated (the acute phase of the infection).

A patient with mild clinical Covid symptoms was treated early during the acute phase of infection after viral PCR SARS-CoV-2 infection confirmation, with Symbicort twice a day—an inhaled corticosteroid (budesonide 160) and long-acting beta2 agonist (formoterol 4.5) from the initial SARS2 rt-PCR positive test, confirming their SARS2 infection. This patient was treated for 2 weeks during the clinical period before and upon discharge as continuously as maintenance for several weeks, after which the medication was then discontinued.

A similar patient but with moderate to severe disease (with markedly elevated CRP LDH and ferritin levels relative to hospital standard reference values) was treated later during the course of their infection after peak clinical severity with Advair 100/50 twice a day—an inhaled corticosteroid (fluticasone) and beta2 agonist (salmeterol) in addition to supportive medications and treatments. This patient was treated during their clinical period and then maintained on this therapy for 6 weeks afterward and then tapered down to an as-needed basis. At 3 and 4 months, respectively, both patients have reported and were noted to have significantly decreased loss in lung function by PFTs relative to others that had not had similar treatments and no evidence of lasting structural change by radiological imaging. In contrast, similar patients, as well as asymptomatic patients, demonstrated volume loss and mild to moderate lung fibrosis, loss in capacity and reserve of 20-30%, and increased exertional dyspnea, fatigue, and apparent hyperreactive airways.

Example 2

Inhaled corticosteroid and Beta2 adrenoreceptor agonist therapy maintain lung function and structure during the post-acute phase, improves lung capacity and exertional tolerance, and mitigates or prevents progressive loss of lung function and pulmonary structure over time due to SARS2. This transition period can be determined in any number of ways, including but not limited to laboratory, blood serum, urine, fecal, sputum, imaging, bronchial lavage, genomic, or tissue-based testing. This transition, typically, though not exclusively, occurs clinically when peak structural findings on imaging (example, chest Xray, CT scan, or MRI) have reduced by around 50% or more from peak severity and/or when laboratory values have trended downwards for 2 successive days and/or are now near or below the upper bounds of normal for ferritin, LDH and CRP, and/or when oxygen requirements and support have diminished by 50% or greater from peak severity/requirement. During this period, pharmacologic agents and combinations as disclosed herein can be administered to limit, contain, improve or restrain inflammatory/immune mediated damage and limit the progression of SARS2 associated lung damage as described above both physiologically, functionally, and structurally. This can be administered in asymptomatic, mild, moderate, and severe SARS2 disease patients.

A patient with mild clinical COVID symptoms was treated at the end of the first week from time of confirmed COVID diagnosis, with Symbicort twice a day—an inhaled corticosteroid (budesonide 160) and long-acting beta2 agonist (formoterol 4.5). This patient was treated for 2 weeks during the clinical period before and upon discharge, after which the medication was then discontinued.

A similar patient was treated on day 10 with Advair 100/50 twice a day—an inhaled corticosteroid (fluticasone) and beta2 agonist (salmeterol). This patient was treated during their clinical period and then maintained on this therapy for 2 weeks afterward and then tapered down to an as-needed basis. At 3 and 4 months, respectively, both patients have reported and were noted to have significantly decreased loss in lung function by PFTs and no evidence of lasting structural change by radiological imaging. In contrast, similar patients, as well as some asymptomatic patients, who were not similarly treated, demonstrated volume loss and mild to moderate lung fibrosis, loss in capacity and reserve of 20-30%, and increased exertional dyspnea and hyperreactive airways.

Example 3

Pirfenidone and Nintedanib therapy during the post-acute phase mitigates functional and structural lung loss, preserves lung function and structure, and can improve lung capacity and exertional tolerance in patients previously infected SARS2 with significant pulmonary functional and structural loss as a result of their severe infections. This transition period can be determined in any number of ways including but not limited to laboratory, blood serum, urine, fecal, sputum, bronchial lavage, imaging, genomic or tissue-based testing. These patients can also be characterized in one embodiment as those patients with prolonged hospitalization due to lung disease, prolonged ventilation, course of ECMO, high peaks during hospitalization 1.5 times above the upper of normal for LDH, or Ferritin, or CRP, >30% loss in pulmonary capacity or pulmonary reserve, significant scarring and/or fibrosis seen by CT imaging, MRI, PET imaging or chest x-ray, significant reductions in physiological and functional measures as assessed by the objective physiologic and functional assessments described above, and/or a progressive or worsening pattern of any of such measures over time. During this period, pharmacologic agents and combinations as disclosed herein can be administered to limit, contain, or restrain or reduce such damage and limit the progression of severe SARS2 associated lung damage as described above both physiologically functionally and structurally. A patient with severe clinical COVID symptoms and severe lung damage, and >40% loss of pulmonary reserve by objective testing was treated with pirfenidone starting 1 month after discharge. At 3 months, an improvement in PFTs and reduction in progression of structural lung damage by high-resolution CT (HRCT) imaging was observed. A similar patient was treated with a 50% loss of pulmonary reserve. Two months post-discharge showed slight structural damage and physiologic testing, and the patient was initiated on nintedanib. At 4 months, both the structural and physiologic declines appeared stabilized and arrested.

Example 4

Ramakrishnan et al., *Inhaled budesonide in the treatment of early COVID-19 illness: a randomized controlled trial*, MEDRXIV PREPRINT, https://doi.org/10.1101/2021.02.04.21251134, last updated Feb. 8, 2021, reported that administrating 800 µg inhaled budesonide twice a day in adults aged 19-79 within seven days of the onset of mild COVID symptoms reduced the likelihood of needing urgent medical care and reduced recovery time.

Budesonide, the active component of PULMICORT TURBUHALER (budesonide) 200 µg, is a corticosteroid designated chemically as (RS)-11β,16α,17,21-tetrahydroxy-pregna-1,4-diene-3,20-dione cyclic 16,17-acetal with butyraldehyde. Budesonide is provided as a mixture of two epimers (22R and 22S). Budesonide is indicated for the maintenance treatment of asthma as prophylactic therapy in adult and pediatric patients six years of age or older. It is also indicated for patients requiring oral corticosteroid therapy for asthma. The starting dose for adults is 200-400 µg BID and going up to 400 µg BID, or starting at 400-800 µg BID and going up to 800 µg BID. The numbers are lower for children, who start at 200 µg or 400 µg BID and are recommended to go up to 400 µg BID. See *Pulmocort Turbuhaler*, https://www.rxlist.com/pulmicort-turbuhaler-drug.htm, (last viewed Mar. 4, 2021).

Patient symptoms were measured through self-reported evaluations, such as the Common Cold Questionnaire (CCQ), a metric developed by the Hunter Medical Research Institute which records general, nasal, throat, and chest cold-like symptoms and scores them based on severity, and the InFLUenza Patient-Reported Outcome (FluPRO®), a 32-item instrument developed by Evidera® that assesses the severity of influenza-like symptoms across the body. Additionally, patient conditions were assessed directly through pulse oximeter readings, body temperatures, and SARS-CoV-2 viral loads obtained with nasopharyngeal swabs by trained clinical staff.

In a study of 70 patients treated with inhaled budesonide only (BUD), one participant required medical intervention. In the control group of 69 patients receiving routine clinical treatments ("usual care," or UC), ten participants required intervention. Patients in the BUD arm self-reported clinical recovery one day quicker than patients in the UC arm. On day 14 of treatment, self-reported symptoms were present in 10% of BUD participants than 30% of UC participants.

The primary outcome occurred in ten participants in the UC arm versus one participant in BUD arm (difference in proportions 0.131, 95% CI (0.043, 0.218), p=0.004), indicating a relative risk reduction of 90% for BUD. Self-reported clinical recovery was 1 day quicker with BUD than UC (median of 7 days versus 8 days, logrank test p=0.007). The mean time to recovery in days was 8 and 11 in the BUD and UC arm, respectively. At day 14, self-reported symptoms were present in 10% (n=7) of participants randomized to BUD compared to 30% (n=21) of participants randomized to UC (difference in proportion 0.204, p=0.003). Symptom resolution at day 14, as defined by the FLUPro® user manual, occurred in 82% and 72% of the BUD and UC arms, respectively (p=0.166). The median time to symptom resolution measured by the FLUPro® was 3 and 4 days in the BUD and UC arms, respectively (logrank test p=0.080). The mean change (95% CI) in FLUPro® total score between day 0 and day 14 in the BUD and UC are −0.65 (−0.80 to −0.50) and −0.54 (−0.69 to −0.40) respectively (mean difference of −0.10, 95% CI of the difference −0.21 to −0.00, p=0.044). FLUPro® domains showed that systemic symptoms were significantly greater in BUD than UC (supplementary table 3). The mean change in CCQ total score between day 0 and day 14 in the BUD and UC was −0.49 (−0.63 to −0.35) and −0.37 (−0.51, −0.24) respectively (mean difference of −0.12 (−0.21 to −0.02), p=0.016). In a 'virtual twin' study design, stochastic simulations demonstrated that the daily odds ratio reached the primary outcome, with BUD reduced by 3000%.

As can be seen, inhaled budesonide reduced the likelihood of requiring urgent care, emergency department consultation, or hospitalization. The inhaled glucocorticoid, budesonide, given for a short duration, may effectively treat early COVID-19 disease in adults. With a relative reduction of 90% of clinical deterioration, this effect is equivalent to the efficacy seen following COVID-19 vaccination. The broad inclusion criteria make this study intervention relevant to health care systems worldwide. A quicker resolution of fever, a known poor prognostic marker in COVID-19, and a faster self-reported and questionnaire reported symptom resolution. Fewer participants had persistent COVID-19 symptoms at 14 and 28 days after budesonide therapy compared to usual care.

Patients treated with budesonide had the less severe disease by self-measurement, 90% reduction in the need for a hospital visit, reduced symptoms, such as fever, fatigue, shortness of breath at 14 and 28 days. This study provides direct clinical support in actual patients for the benefits of inhaled steroids to reduce COVID-induced disease severity and/or sequelae.

Example 5

Arnold et al., *Patient outcomes after hospitalization with COVID-19 and implications for follow-up: results from a prospective UK cohort*, 0 THORAX 1-4 (2020) reported a study of adults aged 18-94 with laboratory-confirmed SARS-CoV-2 infections found that a significant number of individuals experienced persistent symptoms and a decline in health-related quality of life (HRQoL) several months after the initial onset of disease. The symptoms surveyed included fatigue, loss of taste or smell (anosmia), head and body aches, difficulty breathing, sore throat, cough, runny nose, diarrhea, sweats, rash, chills, fevers, and nausea. A total of 177 individuals participated in the survey. Eleven were asymptomatic, 150 experienced mild illness, and 16 had moderate or severe disease requiring hospitalization during the initial infection phase. A group of 21 healthy individuals was simultaneously surveyed to act as a control.

Patients were followed-up with a median of 83 days (IQR 74-88 days) after hospital admission and 90 days (IQR 80-97 days) after COVID-19 symptom onset. Eighty-one (74%) patients reported at least one ongoing symptom: 39% breathlessness, 39% fatigue, and 24% insomnia (see figure 1). Sixteen (59%) patients in the mild COVID-19 group reported ongoing symptoms compared with 49 (75%) and 16 (89%) in the moderate and severe group, respectively.

Of the 15/110 (14%) patients with abnormal follow-up radiographs (n=10 moderate group, n=5 severe group), two worsened from hospital admission with higher radiographic severity scores (both had known previous interstitial lung disease). Findings seen included consolidation (one patient), reticulation (eight patients), atelectasis (collapsed lung, five patients), and pleural effusion (one patient). Nine patients showed fibrotic changes in two patients with moderate disease at baseline (other HRCT results: normal (four), minor persistent ground glass changes (two), pleural effusion (one)). Eleven patients had restrictive spirometry, and fifteen had a significant desaturation on the STS test, all within the severe or moderate group (see the online supplementary material). SF-36 scores demonstrated a reduction in reported health status across all domains compared with age-matched population norms.

The follow-up survey was completed in a median range of 169 days (31-300 days) after the initial onset. Persistent symptoms were reported by about 30% of individuals. Patients aged 65 and older reported persistent symptoms at a slightly higher rate (43.3%). The most common symptoms were fatigue (13.6%) and anosmia (13.6%). A total of 51 outpatients and hospitalized patients (30.7%) reported worse HRQoL than baseline versus four healthy/asymptomatic patients (12.5%). These findings support that there is a persistent sequalae after COVID-19 infection, even in mild and asymptomatic cases, as far out as 6 months compared to healthy controls.

Example 6

Logue et al., *Sequelae in Adults at 6 Months After COVID-19 Infection,* 4 JAMA NETWORK OPEN 1-4 (2021), available at https://jamanetwork.com/journals/jamanetworkopen/fullarticle/2776560 reported a study of adults aged 32-71 in the UK with laboratory-confirmed SARS-CoV-2 infections which required hospitalization found that a significant proportion remained symptomatic 3 months following diagnosis. Patients were recruited at diagnosis and had their baseline demographics, comorbidities, and blood test results recorded. Follow-up was performed at a respiratory outpatient clinic 8-12 weeks after hospital admission. Chest radiographs, spirometry, exercise testing, blood tests, and quality-of-life and mental-wellbeing questionnaires were administered to determine the severity and nature of any abnormalities. Patients were subdivided into groups based on the severity of their disease (mild, moderate, or severe).

Out of 110 patients, 81 (74%) reported at least one ongoing symptom. The most common were fatigue (39%), breathlessness (39%), and insomnia (24%). The likelihood of ongoing symptoms increased proportionally to the severity of illness. Fifteen patients presented with abnormal radiographs on follow-up, with two worsening their initial condition at hospitalization. Eleven patients had restrictive spirometry, and fifteen showed significant desaturation upon exercise testing, all from within the moderate and severe illness groups. Blood testing revealed that 35 patients with significantly deranged liver and renal functions at admission had mostly (91%) returned to baseline at follow-up. Health-related quality-of-life (HRQoL) scores were reduced in all domains compared with age-matched population norms.

Example 7

Huang et al., *6-month consequences of COVID-19 in patients discharged from hospital: a cohort study,* 367 THE LANCET 220-232 (2021) reported a cohort study of adults aged 47-65 in Wuhan, Hubei, China with laboratory-confirmed SARS-CoV-2 infections which required hospitalization found that a significant number of patients displayed ongoing symptoms six months after initial onset. Patients were recruited from those discharged from Jin Yin-tan Hospital between Jan. 7, 2020, and May 29, 2020. Follow-up visits were performed at the outpatient clinic of Jin Yin-tan Hospital.

All patients were interviewed with a series of questionnaires to evaluate symptoms and HRQoL, underwent physical examinations and a walking test and received blood tests. Additionally, a stratified sampling procedure was used to select patients based on the severity of their disease to undergo pulmonary function tests, ultrasounds, and high-resolution chest computerized tomography (CT) scans. Patients who were enrolled in the Lopinavir Trial for Suppression of SARS-CoV-2 in China (LOTUS China) tested the effects of lopinavir-ritonavir treatment on clinical recovery time received SARS-CoV-2 antibody tests.

In total, 1733 patients were enrolled in the study, 76% reported at least one symptom at follow-up. Fatigue or muscle weakness (63%), sleep difficulties (26%), and hair loss (22%) were the most common reported symptoms. Anxiety or depression was reported among 23% of patients. Six-minute walking test showed that 23% of patients presented with a shorter walked distance than the lower limit of the normal range for their age group. Pulmonary function tests showed that patients with the most severe disease (those requiring high-flow nasal cannulas or ventilation) displayed a much higher rate of diffusion impairment (56%) than those who did not (27%). Chest CT scans revealed that about half (53%) of all patients displayed at least one abnormal CT pattern, with overall CT scores increasing proportionally with the severity of the disease. Of the 94 patients enrolled in the LOTUS China trial, the seropositivity and median titers of their neutralizing blood antibodies were significantly lower at follow-up (58.5% and 10.0, respectively) than they were during the acute phase (96.2% and 19.0, respectively).

A considerable proportion of participants (22-56% across different severity scales) had a pulmonary diffusion abnormality 6 months after symptom onset. This finding was consistent with the most common abnormal CT pattern was a pulmonary interstitial change (GGOs and irregular lines), which were similar to the long-term lung manifestations of SARS27 or influenza. However, the results from the Huang study did not suggest that corticosteroids could accelerate the recovery of lung injury based on the pulmonary function assessment or chest imaging.

Example 8

A study of adults with a median age of 49 years (IQR 27 years) with COVID-19 from Hong Kong found that over half of patients with asymptomatic or mild cases demonstrated chest radiograph (CXR) abnormalities during active infection. These findings were also directly correlated with baseline reverse transcriptase-polymerase chain reaction (RT-PCR) SARS-CoV-2 testing at diagnosis. As measured by RT-PCR cycle threshold values, patients with higher viral loads were at significantly greater risk for these sequelae at 3 months post viral recovery.

Study participants were RT-PCR positive patients who recovered from SARS-CoV-2 infection between February and August 2020. These patients had clinical and CXR evaluations at initial diagnosis, during isolation with the active infection, and at ≥3 months after recovery and hospital discharge. The 3-month follow-up consisted of an outpatient clinic visit with face-to-face evaluation by a healthcare professional completed ≥3 months after recovery and discharge. Specific symptoms reported at this follow-up visit and diagnosis and upon recovery were recorded. CXRs performed in either posteroanterior or anteroposterior projections within 24 hours of the initial positive RT-PCR test, during an active infection, and at 3-month outpatient, follow-up was used for analyses.

COVID-19 clinical severity was assessed at initial presentation using an ordinal scale recommended by the World Health Organization's (WHO) R&D Blueprint expert group. The ordinal scale categories are: 0=no clinical or virological evidence of infection; 1=no limitations of activities; 2=limitation of activities; 3=hospitalized but not requiring oxygen therapy; 4=hospitalized and requiring oxygen by mask or nasal prongs; 5=requiring non-invasive ventilation or use of high-flow oxygen; 6=requiring intubation and mechanical ventilation; 7=requiring ventilation and additional organ support; and 8=death. For this study, a score of ≤3 was defined as a mild or asymptomatic disease. The 3-month follow-up consisted of an outpatient clinic visit with face-to-face evaluation by a healthcare professional completed ≥3 months after recovery and discharge. Specific symptoms reported at this follow-up visit and at diagnosis and upon recovery were recorded.

In total, 168 patients fulfilled the study criteria. Twenty-two patients (13.1%) were asymptomatic at presentation, of which 20 remained asymptomatic throughout their entire course of viral infection. The most common symptoms at diagnosis were respiratory symptoms (58.9%) for symptomatic patients, such as cough and fever (42.3%). At the 3-month follow-up, 22 (13.1%) patients had persistent symptoms, with respiratory symptoms being the most common (45.5%). Of these 22 patients, 15 (68%) had RT-PCR cycle threshold values <25 at initial diagnosis, indicating a high initial viral load.

During the active infection phase, 85 (50.6%) of patients eventually presented with abnormal CXRs. At the 3-month follow-up, 20 (11.9%) patients had persistent abnormal CXR findings. Three of the 22 (13.6%) asymptomatic patients at diagnosis had persistent CXR abnormalities at 3 months, accounting for 3 (15.0%) out of the 20 patients with abnormal 3-month follow-up CXRs. All 20 of the patients with abnormal 3-month CXRs also had abnormal CXRs during the active infection phase.

In summary, about 12% of all patients had persistent abnormalities and symptoms three months after initial recovery from the viral infection. About 50% of mild and asymptomatic COVID-19 patients had abnormal CXRs during active infection. Twenty-five percent of the mild and asymptomatic patients with an abnormal CXR at diagnosis were found to have persistent CXR abnormalities at 3-month follow-up. An RT-PCR cycle threshold value <25 and a maximum CXR severity score of greater the one predicted the symptoms and CXR abnormalities at 3-month follow-up, respectively.

No correlation was identified between initial RT-PCR cycle threshold values and CXR findings at the 3-month follow-up. Indeed, only two of the twelve mild and asymptomatic COVID-19 patients treated with steroids during active infection went on to have persistent symptoms three months after the initial viral recovery. Similarly, only three of the twelve patients with moderate or severe infection who were treated with steroids went on to have persistent abnormalities, suggesting that the lungs were damaged in both patient groups, as shown in the chest imaging at three months post viral.

Post COVID-19 patients did not express asthma or post-viral reactive airways. None of the preceding examples described their findings with the typical words or phrases consistent with asthma-fatigue, exertional dyspnea, shortness of breath, hyperreactive airways, bronchospasm, or other physical descriptions of a patient with asthma or COPD. Thus, based on the patients' symptoms alone, a physician would not have considered using inhaled steroids to treat the symptoms of the virus during infection or after the initial recovery.

It is also generally known and well-accepted that one should not dose patients with inhaled steroids who did not have asthma or COPD. A prominent reason is the side effects of chronic use. For example, Hanania, N. et al., *Adverse Effects of Inhaled Corticosteroids*, 98 AM. J. MED. 196-208 (1995) states that while inhaled steroids can treat asthma, they should be minimized in use and dose because of the side effects, including adrenal suppression, bone loss, skin thinning, increased cataract formation, decreased linear growth in children, metabolic changes, and behavioral abnormalities.

Another reason is the inability of inhaled steroids to effectively treat acute viral respiratory tract infections, even in a patient with asthma. Doull, I J M et al., *Effect of inhaled corticosteroids on episodes of wheezing associated with viral infection in school age children: randomised double blind placebo controlled trial*, 315 BMJ doi: https://doi.org/10.1136/bmj.315.7112.858 (last updated Oct. 4, 1997) reports a study that shows no clear benefit for inhaled steroids in kids with asthma and viral infection for reducing virus-associated wheezing. Systemic corticosteroids decreased the illness associated with such wheezing in adults, but in younger children, inhaled corticosteroids offered minimal benefits, either when given at the onset of symptoms or continuously. Thus, before learning the treatment methods disclosed herein, a person having skill in the art would not have treated a subject for a pulmonary disease or symptom which is the consequence of previous exposure of the subject to SARS-CoV-2 by administering to the subject of an effective amount of one or more corticosteroids, such as inhaled budesonide.

The detailed description set-forth above is provided to aid those skilled in the art in practicing the present disclosure. However, the disclosure described and claimed herein is not limited in scope by the specific embodiments herein disclosed because these embodiments are intended to illustrate several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references to patents, patent documents, articles, and internet citations are incorporated by references in their entireties for all purposes.

What is claimed is:

1. A method of treating dyspnea, shortness of breath, fatigue, cough, chest pain, and combinations thereof, which is a pulmonary sequela of a subject who had COVID-19, the method comprising administering to the subject in need thereof an effective amount of one or more corticosteroids.

2. The method of claim 1, wherein the one or more corticosteroids are chosen from hydrocortisone, methylprednisolone, budesonide, beclomethasone, fluticasone, fluticasone furoate, fluticasone propionate, mometasone, mometasone furoate, and vamorolone.

3. The method of claim 2, wherein the one or more corticosteroids is budesonide.

4. The method of claim 2, wherein the one or more corticosteroids is administered twice daily.

5. The method of claim 1, wherein the one or more corticosteroids are administered continuously for a period of time.

6. The method of claim 1, wherein the one or more corticosteroids are administered when the subject expresses the sequela or before the subject partakes in an activity that may precipitate the sequela.

7. The method of claim 1 further comprising administering one or more leukotriene antagonists.

8. The method of claim 7, wherein the one or more leukotriene antagonists are chosen from zafirlukast, montelukast, and zileuton.

9. The method of claim 1 further comprising administering one or more beta-agonists.

10. The method of claim 1 further comprising administering one or more methylxanthines.

11. The method of claim 10, wherein the methylxanthine is chosen from theophylline, dyphylline, and aminophylline.

12. The method of claim 1 further comprising administering one or more bronchodilators.

13. The method of claim 12, wherein the one or more bronchodilators comprises an anticholinergic.

14. The method of claim 8, wherein the one or more bronchodilators comprises an antimuscarinic.

15. The method of claim 14, wherein the antimuscarinic is chosen from tiotropium, ipratropium, aclidinium, glycopyrronium, and/or salts thereof.

16. The method of claim 12, wherein the one or more bronchodilators comprises a beta-2 agonist.

17. The method of claim 16, wherein the beta-2 agonist is chosen from salbutamol, albuterol, salmeterol, and formoterol.

18. The method of claim 1, wherein exposure of the subject to SARS-CoV-2 virus is confirmed by a positive titer for the SARS-CoV-2, by a positive titer for antibodies to the SARS-CoV-2, or by one or more recognized clinical symptoms associated with infection by SARS-CoV-2.

19. The method of claim 1, wherein the subject is treated six days after initial recovery from SARS-CoV-2.

20. The method of claim 1, wherein the subject is treated one year after initial recovery from SARS-CoV-2.

21. The method of claim 1, wherein the pulmonary sequela is caused by a loss in pulmonary function and/or a change in pulmonary structure from the SARS-CoV-2 infection.

22. The method of claim 21, wherein the loss of pulmonary function is characterized by a pulmonary flow test (PFT) and a six-minute walk test (6MWT) and the change in pulmonary structure is characterized by chest X-ray or computerized tomography.

* * * * *